(12) United States Patent
Ammon

(10) Patent No.: US 8,975,228 B2
(45) Date of Patent: Mar. 10, 2015

(54) USE OF BOSWELLIC ACIDS FOR THE PROPHYLAXIS AND/OR TREATMENT OF DAMAGE TO AND/OR INFLAMMATION OF THE ISLETS OF LANGERHANS

(75) Inventor: Hermann P. T. Ammon, Tübingen (DE)

(73) Assignee: Fraunhofer-Gesellschaft zur Forderung der Angewandten Forschung E.V., München (DE)

( * ) Notice: Subject to any disclaimer, the term of this patent is extended or adjusted under 35 U.S.C. 154(b) by 0 days.

(21) Appl. No.: 13/240,972

(22) Filed: Sep. 22, 2011

(65) Prior Publication Data

US 2012/0070497 A1 Mar. 22, 2012

Related U.S. Application Data

(60) Provisional application No. 61/385,468, filed on Sep. 22, 2010.

(30) Foreign Application Priority Data

Sep. 22, 2010 (EP) .................................... 10178222

(51) Int. Cl.
| | |
|---|---|
| *A61K 9/36* | (2006.01) |
| *A61K 31/19* | (2006.01) |
| *A61K 38/21* | (2006.01) |
| *A61K 31/522* | (2006.01) |
| *A61K 31/4406* | (2006.01) |
| *A61K 31/215* | (2006.01) |
| *A61K 31/7028* | (2006.01) |
| *A61P 1/18* | (2006.01) |
| *A61P 3/10* | (2006.01) |
| *A61P 29/00* | (2006.01) |
| *C07C 69/013* | (2006.01) |
| *C07C 62/38* | (2006.01) |

(52) U.S. Cl.
CPC ..................................... *A61K 31/19* (2013.01)
USPC ........... 514/12.2; 514/6.7; 514/510; 514/557; 424/479

(58) Field of Classification Search
USPC ..................................... 424/400; 514/54, 170
See application file for complete search history.

(56) References Cited

U.S. PATENT DOCUMENTS

| | | | |
|---|---|---|---|
| 2003/0017148 A1 | 1/2003 | Tabatabaie et al. | |
| 2003/0215439 A1 * | 11/2003 | Dietsch et al. | 424/94.63 |
| 2005/0282772 A1 * | 12/2005 | Gokaraju et al. | 514/54 |
| 2006/0148732 A1 | 7/2006 | Gutterman et al. | |
| 2006/0234990 A1 * | 10/2006 | Majeed et al. | 514/170 |
| 2007/0048246 A1 * | 3/2007 | Sovak et al. | 424/74 |

FOREIGN PATENT DOCUMENTS

| | | |
|---|---|---|
| DE | 100 35 591 A1 | 1/2002 |
| WO | WO 03/077860 A2 | 9/2003 |
| WO | WO 2008/065666 A2 | 6/2008 |
| WO | WO 2010/029578 A2 | 3/2010 |

OTHER PUBLICATIONS

Scarpello et al., "Metformin therapy and clinical uses". Diabetes and Vascular Disease Research 2008 5 (3);157-167.*
H.P.T Ammon, "Salai Guggal—Boswellia serrata: from a herbal medicine to a specific inhibitor of leukotriene biosynthesis" Phytomedicine 3(1):1996;67-70.*
Descamps et al., "Gelatinase B is diabetogenic in acute and chronic pancreatitis by cleaving insulin" The FASEB Journal experss article 10.1096/fj.02-0725fje. Published online Mar. 5, 2003; 13 pages.*
In't Veld, "Insulitis in Type 1 Diabetes: A Sticky Problem" Diabetes vol. 58, Jun. 2009;1257-1258.*
Boni-Schnetzler et al., "Insulitis in type 2 diabetes", Diabetes Obes Metab., Nov. 10. 2008 Suppl 4:201-4.
Donath MY, "Islet inflammation in type 2 diabetes: from metabolic stress to therapy", Diabetes Care, Feb. 2008:31 Suppl 2:S161-4.
Donath MY, "Islet inflammation impairs the pancreatic beta-cell in type 2 diabetes", Physiology (Bethesda), Dec. 2009; 24:325-31.
Ehses et al., "Macrophages, cytoldnes and beta-cell death in Type 2 diabetes" Biochem Soc Trans, Jun. 2008; 36(Pt 3):340-2.
Ammon, H.P.T. (2006) Boswellic Acids in Chronic Inflammatory Diseases, Planta Med, 77: 1100-1116.
Büchele, Zugmaler, and Simmet (2003) J Chromatogr B, 791: 21-30.
Helal, Mostafa, Ashour and Kahwash (2005) Effect of Boswellia Carterii Birdw on Carbohydrate Metabolism in Diabetic Male Albino Rats, The Egyptian Journal of Hospital Medicine, vol. 20: 38-45.
Helal and Abbas (2006) Effect of some herbal medicine on some biochemical parameters in diabetic rats, The Egyptian Journal of Hospital Medicine, vol. 22: 98-110.
Kavitha et al. (2007) Hypoglycemic and other related effects of Boswellia glabra in Alloxan-induced diabetes rats, Indian J Physiol Pharmacol, 51 (1): 29-39.
Papi Reddy K et al. (2009) Synthesis of novel triterpenoid (lupeol) derivatives and their in vivo antihyperglycemic and antidyslipidemic activity, Bioorganic & Medicinal Chemistry Letters, LNKD-PUBMED: 19515563, vol. 19, No. 15, pp. 4463-4466.

(Continued)

*Primary Examiner* — Walter Webb
(74) *Attorney, Agent, or Firm* — Knobbe Martens Olson & Bear LLP

(57) ABSTRACT

Disclosed are methods and compositions related to the use of boswellic acids (such as acetyl-11-keto-β-boswellic acid, 11-keto-β-boswellic acid, β-boswellic acid, acetyl-β-boswellic acid, 9,11-dehydro-β-boswellic acid, acetyl-9,11-dehydro-β-boswellic acid, α-boswellic acid, acetyl-α-boswellic acid, 11-dehydro-α-boswellic acid, acetyl-9,11-dehydro-α-boswellic acid, lupeolic acid, acetyl lupeolic acid, 12-ursene-2-diketone, incensole, incensole acetate, a derivative, in particular an ester thereof, a pharmaceutically acceptable salt thereof, a combination thereof, or a preparation containing one or more of these compounds) for the human medical or veterinary prophylaxis and/or treatment of: a) damage to and/or inflammation of the islets of Langerhans and/or b) damage to the B-cells of the islets of Langerhans.

19 Claims, 29 Drawing Sheets

(56) References Cited

OTHER PUBLICATIONS

Singh et al. (1993) G.B. Singh, Boswellic Acids, Drugs of the Future, 18: 307-309.

51st Annual Meeting Deutsche Gesellschaft fur Experimentelle und Klinische Pharmakologie und Toxikologie Mainz, Mar. 23 to 25, 2010, Naunyn-Schmiedeberg'S Archives of Pharmacology, Springer, Berlin, DE, vol. 381, No. 1, Mar. 24, 2010, pp. 1-92.

* cited by examiner

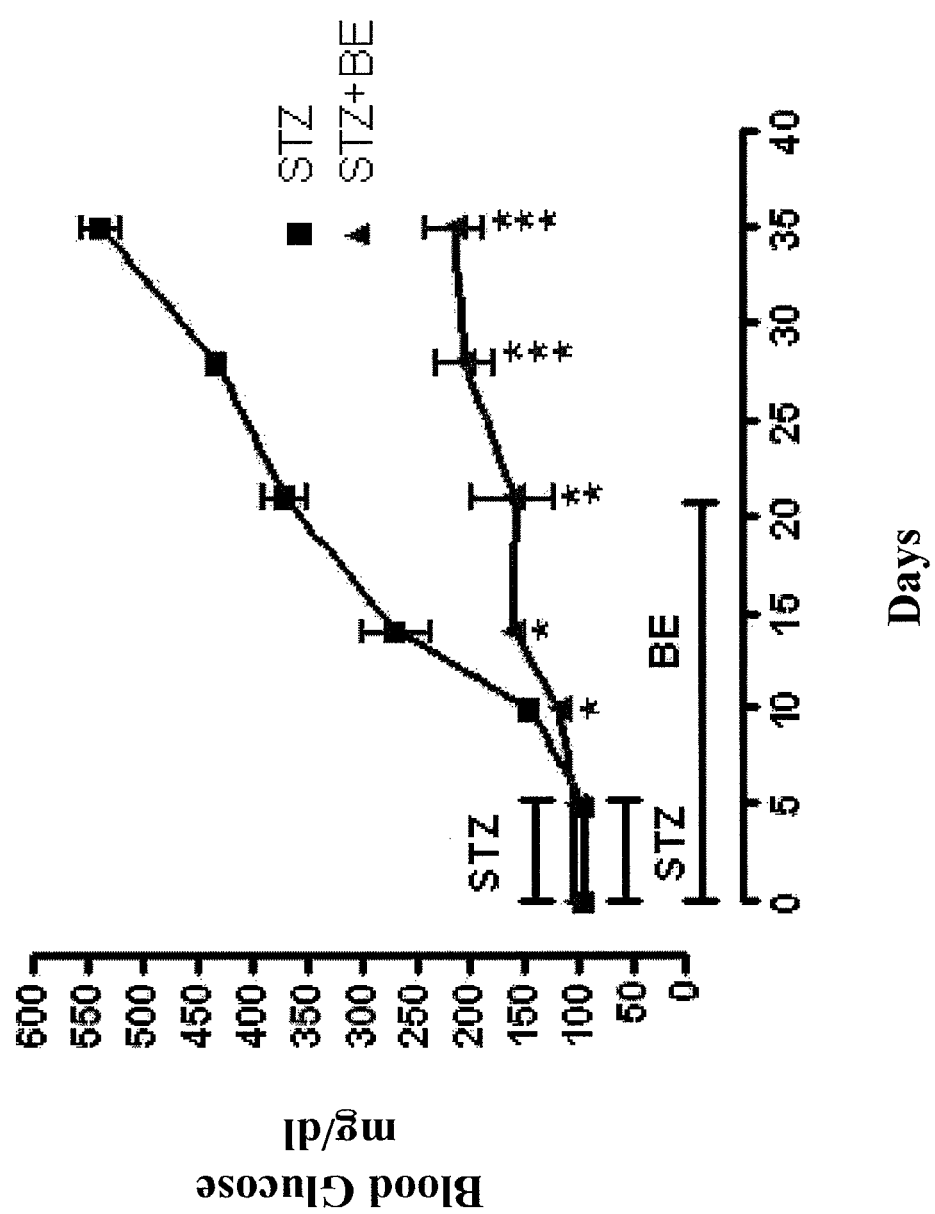

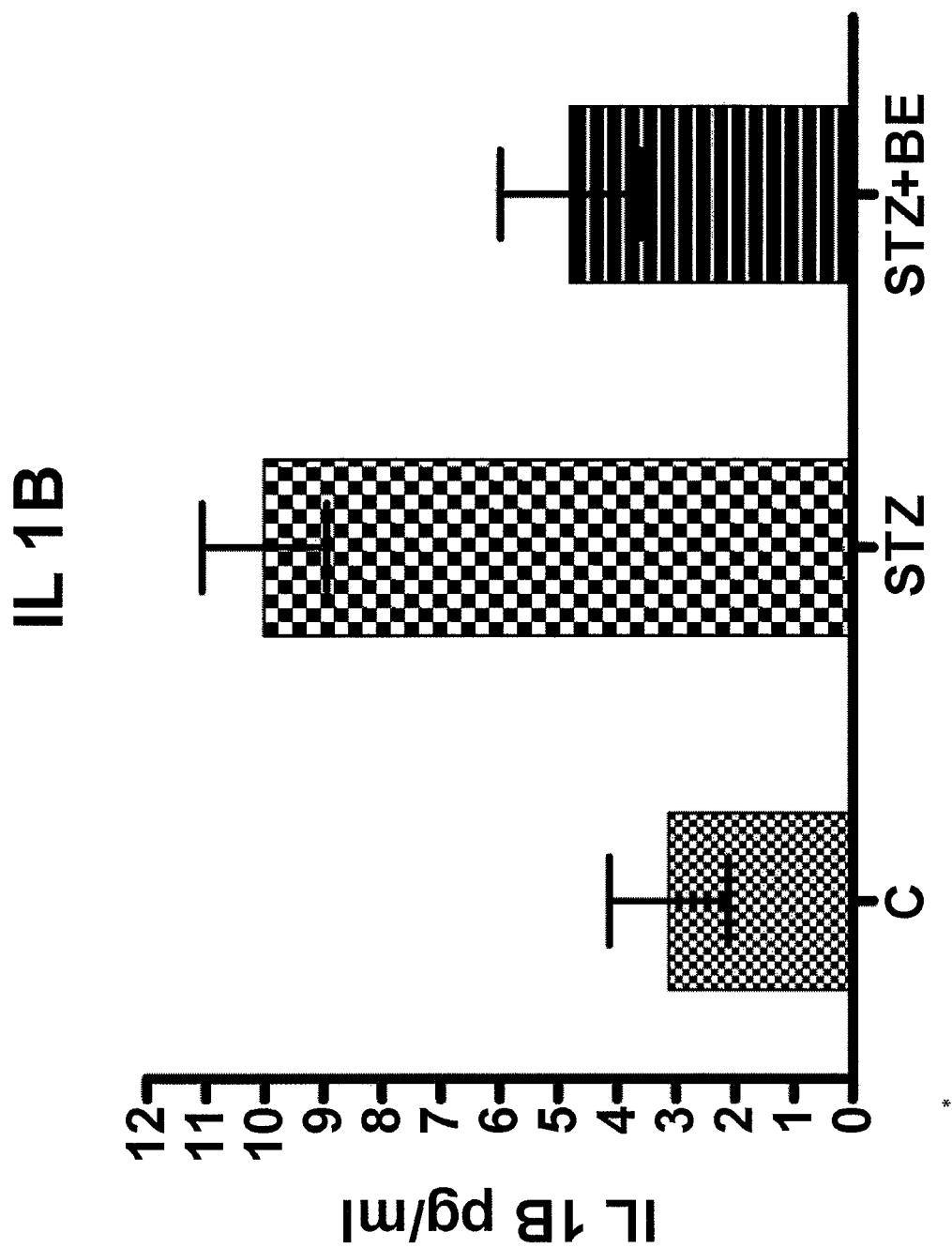

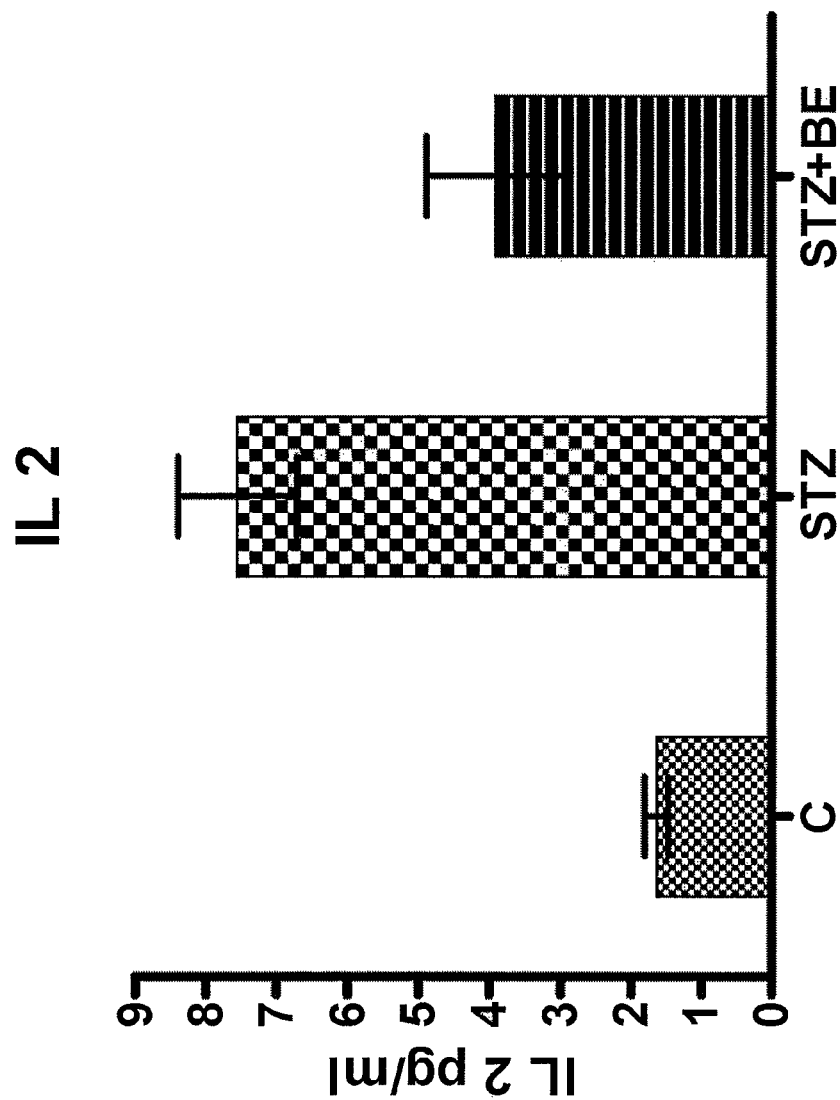

USE OF BOSWELLIC ACIDS FOR THE PROPHYLAXIS AND/OR TREATMENT OF DAMAGE TO AND/OR INFLAMMATION OF THE ISLETS OF LANGERHANS

REFERENCE TO RELATED APPLICATIONS

This application claims priority under 35 U.S.C. §119(e) to U.S. Provisional Patent Application Ser. No. 61/385,468, filed on Sep. 22, 2010, and under 35 U.S.C. §119(b) to European Application No. EP 1017822.5, filed on Sep. 22, 2010, which are each incorporated herein by reference in their entireties.

FIELD OF THE INVENTION

The present invention relates to the use of boswellic acids as well as to preparations containing boswellic acids for human medical or veterinary prophylaxis and/or the treatment of damage and/or inflammation of the islets of Langerhans and/or damage of the B-cells of the islets of Langerhans. In particular, the methods described herein relate to the use of boswellic acids as well as preparations containing boswellic acid(s) for the human medical or veterinary prophylaxis and/or the treatment of damage and/or inflammation of the islets of Langerhans and/or damage of B-cells of the islets of Langerhans, wherein the damage is accompanied by inflammation (insulitis). Preferably, the damage and/or inflammation of the islets of Langerhans and/or of the B-cells of the islets of Langerhans is/are associated with type 1 diabetes, type 2 diabetes or pancreatitis.

BACKGROUND

There are two main types of diabetes. Type 1 diabetes (or "juvenile diabetes") is caused by an absolute insulin deficiency as a result of damaged B cells or B cell death that is frequently associated with insulitis. Type 2 diabetes (or "adult onset diabetes") is principally caused by an insulin resistance of the tissue. This insulin resistance is accompanied by relative insulin deficiency and increased glucose production in the liver. In many cases, type 2 diabetes is also accompanied by insulitis. Cellular damage or inflammation of the islets of Langerhans of the pancreas can impair the functioning of the insulin-producing B cells or lead to a complete loss of function due to B cell death. This results in an absolute insulin deficiency, which causes insulin-depending diabetes mellitus (IDDM). IDDM mainly occurs in children, youths or adolescents. However, it can also demonstrate onset in advanced age. In this case, it is called "latent autoimmune diabetes of the adult" (LADA).

The most important aspect of inflammation of the islets of Langerhans is an infiltration by macrophages and T-lymphocytes. During the activation of the TH1-lymphocytes, B cells can be destroyed due to apoptosis resulting in the progression of the disease. The apoptosis does not affect the A cells or D cells (the glucagon of the A cells increases the blood glucose level, and the somatostatin of the D cells inhibits the secretion of insulin).

Without insulin substitution, this condition eventually leads to death due to diabetic coma. Previous attempts to suppress the course of the diabetic disease, e.g. by administering anti-inflammatory agents such as non-steroidal antiphlogistic agents, glucocorticoids (the latter even having a diabetogenous effect), immunosuppressants, or by immune intervention and immune prevention, e. g. by administering cyclosporine A, have not led to a satisfactory solution. In fact, these therapeutic attempts have rather considerable side effects. Other therapeutic approaches such as the treatment with methotrexate, nicotinamide, monoclonal antibodies, azothioprine etc. have not proven to be suited either to influence damage of B-cells in a way that is efficient for the diabetic person with little side effects. Neither has the use of anti-inflammatory agents that act selectively such as COX2-inhibitors (US 2003/0017148) led to success.

SUMMARY OF THE INVENTION

In one embodiment, a method of ameliorating inflammation of the islets of Langerhans in a subject is provided, comprising administering to the subject a composition comprising a compound selected from the group consisting of acetyl-11-keto-β-boswellic acid, 11-keto-β-boswellic acid, β-boswellic acid, acetyl-β-boswellic acid, 9,11-dehydro-β-boswellic acid, acetyl-9,11-dehydro-β-boswellic acid, α-boswellic acid, acetyl-α-boswellic acid, 11-dehydro-α-boswellic acid, acetyl-9,11-dehydro-α-boswellic acid, lupeolic acid, acetyl-lupeolic acid, 12-ursene-2-diketone, incensole, incensole acetate, derivatives thereof, esters thereof, pharmaceutically acceptable salts thereof, and combinations thereof.

In one aspect of this embodiment, the inflammation of the islets of Langerhans is associated with a condition selected from the group consisting of type 1 diabetes, type 2 diabetes, and pancreatitis. In another aspect of this embodiment, the type 1 diabetes is a subtype selected from the group consisting of type 1a diabetes, LADA diabetes, and type 1b diabetes. In a further aspect of this embodiment, the composition consists of acetyl-11-keto-β-boswellic acid or a pharmaceutically acceptable salt thereof and 11-keto-β-boswellic acid or a pharmaceutically acceptable salt thereof. In a further aspect of this embodiment, the composition is in a single dosage form. In a further aspect of this embodiment, the single dosage form is formulated for intraperitoneal, oral, buccal, rectal, intramuscular, subcutaneous or intravenous administration. In a further aspect of this embodiment, the single dosage form is a tablet, sugar coated tablet, capsule, solution, emulsion, or suppository. In a further aspect of this embodiment, the composition further comprises at least one other pharmaceutical substance. In a further aspect of this embodiment, the at least one other pharmaceutical substance is selected from the group consisting of an antiphlogistic, an oral antidiabetic, an antioxidant, pentoxifylline, isoxazolene, an interferon, a ganglioside, an α-adrenoceptor antagonist, nicotinamide, dimethylurea, a lipid-lowering agent, and an herbal drug. In a further aspect of this embodiment, the oral antidiabetic is selected from the group consisting of a sulfonylurea, a glinide, metformin, an imidazolidinone, a glitazone, an α-glucosidase inhibitor, and a dipeptylpeptidase IV inhibitor. In a further aspect of this embodiment, the subject is: i) a person with a genetic predisposition for type 1 diabetes and a diabetes-inducing disease caused by a virus selected from the group consisting of mumps virus, coxsackie B virus, rubella virus, measles virus, cytomegalovirus, and influenza virus; ii) a person with at least one type 1 diabetic parent or sibling; or iii) a person with at least one upregulated diagnostic marker for inflammation of the pancreas. In a further aspect of this embodiment, the diagnostic marker is selected from the group consisting of a glutamate decarboxylase, a tyrosine phosphatase IA-2, and an islet cell antibody, In another embodiment, a composition for the amelioration of inflammation of the islets of Langerhans is provided, comprising at least one isolated compound selected from the group consisting of acetyl-11-keto-β-boswellic acid, 11-keto-β-boswellic acid, β-boswellic acid, acetyl-13-boswellic acid, 9,11-dehydro-3-boswellic acid, acetyl-9,11-dehydro-β-boswellic acid, α-boswellic acid, acetyl-α-boswellic acid, 11-dehydro-α-boswellic acid, acetyl-9,11-dehydro-α-boswellic acid, lupeolic acid, acetyl-lupeolic acid, 12-ursene-2-diketone, incensole, incensole acetate, derivatives thereof, esters thereof, pharmaceutically acceptable salts thereof, and combinations thereof.

In one aspect of this embodiment, the composition consists of acetyl-11-keto-β-boswellic acid or a pharmaceutically acceptable salt thereof and 11-keto-β-boswellic acid or a pharmaceutically acceptable salt thereof. In another aspect of this embodiment, the acetyl-11-keto-α-boswellic acid or pharmaceutically acceptable salt thereof and the 11-keto-β-boswellic acid or pharmaceutically acceptable salts thereof are contained in a single dosage form. In a further aspect of this embodiment, the single dosage form is formulated for intraperitoneal, oral, buccal, rectal, intramuscular, subcutaneous, or intravenous administration. In a further aspect of this embodiment, the single dosage form is a tablet, sugar-coated tablet, capsule, solution, emulsion, or suppository. In a further aspect of this embodiment, the composition further comprises at least one other pharmaceutical substance. In a further aspect of this embodiment, the at least one other pharmaceutical substance is selected from the group consisting of an antiphlogistic, an oral antidiabetic, an antioxidant, pentoxifylline, isoxazolene, an interferon, a ganglioside, an α-adrenoreceptor antagonist, nicotinamide, dimethylurea, a lipid-lowering agent, and an herbal drug. In a further aspect of this embodiment, the oral antidiabetic is selected from the group consisting of a sulfonylurea, a glinide, metformin, an imidazolidinone, a glitazone, an α-glucosidase inhibitor, and a dipeptylpeptidase IV inhibitor.

In further embodiment, acetyl-11-keto-β-boswellic acid, 11-keto-β-boswellic acid, β-boswellic acid, acetyl-β-boswellic acid, 9,11-dehydro-β-boswellic acid, acetyl-9,11-dehydro-β-boswellic acid, α-boswellic acid, acetyl-α-boswellic acid, 11-dehydro-α-boswellic acid, acetyl-9,11-dehydro-α-boswellic acid, lupeolic acid, acetyl-lupeolic acid, 12-ursene-2-diketone, incensole, incensole acetate, a derivative, in particular an ester thereof, a pharmaceutically acceptable salt thereof, a combination thereof, or a preparation containing one or more of these compounds is provided for human medical or veterinary prophylaxis and/or treatment of a) damage to or inflammation of the islets of Langerhans and/or b) damage to B-cells of the islets of Langerhans.

In one aspect of this embodiment, the damage to the islets of Langerhans and/or their B-cells is accompanied by inflammation (insulitis). In another aspect of this embodiment, the damage to and/or the inflammation of the islets of Langerhans and/or the damage to the B-cells is/are associated with type 1 diabetes, type 2 diabetes or pancreatitis. In a further aspect of this embodiment, the type 1 diabetes is type 1a diabetes, LADA diabetes or type 1b diabetes. In a further aspect of this embodiment, the combination consists of acetyl-11-keto-β-boswellic acid and 11-keto-β-boswellic acid and/or pharmaceutically acceptable salts thereof. In a further aspect of this embodiment, acetyl-11-keto-β-boswellic acid and 11-keto-β-boswellic acid are contained in a composition. In a further aspect of this embodiment, use is made intraperitoneally, orally, buccally, rectally, intramuscularly, subcutaneously or intravenously. In a further aspect of this embodiment, use is made in the form of tablets, sugar coated tablets (dragees), capsules, solutions, emulsions or suppositories. In a further aspect of this embodiment, use is made together with at least one other pharmaceutical substance. In a further aspect of this embodiment, the oral antidiabetic is selected from sulfonylureas, glinides, metformin, imidazolidinones, glitazones, α-glucosidase inhibitors, and dipeptylpeptidase IV inhibitors. In a further aspect of this embodiment, the person receiving prophylaxis and/or treatment is selected from: i) genetically predisposed persons with preceding diabetes-inducing diseases caused by viruses, said viruses selected from mumps viruses, coxsackie B viruses, rubella viruses, measles viruses, cytomegaloviruses, and influenza viruses, and/or ii) persons with at least one type 1 diabetic parent or sibling, and/or iii) persons with up-regulated diagnostic markers for inflammation of the pancreas. In a further aspect of this embodiment, the diagnostic marker is selected from glutamate decarboxylase (glutamic acid decarboxylase), tyrosine phosphatase IA-2, and islet cell antibodies (ICA)

In a further embodiment, use of acetyl-11-keto-β-boswellic acid, 11-keto-β-boswellic acid, β-boswellic acid, acetyl-β-boswellic acid, 9,11-dehydro-β-boswellic acid, acetyl-9,11-dehydro-β-boswellic acid, α-boswellic acid, acetyl-α-boswellic acid, 11-dehydro-α-boswellic acid, acetyl-9,11-dehydro-α-boswellic acid, lupeolic acid, acetyl-lupeolic acid, 12-ursene-2-diketone, incensole, incensole acetate, a derivative, in particular an ester thereof, a pharmaceutically acceptable salt thereof, a combination thereof, or a preparation containing one or more of these compounds for the preparation of a pharmaceutical drug is provided for human medical or veterinary prophylaxis and/or treatment of: a) damage to and/or inflammation of the islets of Langerhans and/or b) damage to the B-cells of the islets of Langerhans.

In one aspect of this embodiment, the damage to the islets of Langerhans and/or their B-cells is accompanied by inflammation (insulitis). In another aspect of this embodiment, the damage to and/or the inflammation of the islets of Langerhans and/or the damage to the B-cells is/are associated with type 1 diabetes, type 2 diabetes or pancreatitis. In a further aspect of this embodiment, the type 1 diabetes is type 1a diabetes, LADA diabetes or type 1b diabetes. In a further aspect of this embodiment, the combination consists of acetyl-11-keto-β-boswellic acid and 11-keto-β-boswellic acid and/or pharmaceutically acceptable salts thereof. In a further aspect of this embodiment, acetyl-11-keto-β-boswellic acid and 11-keto-β-boswellic acid are contained in a composition. In a further aspect of this embodiment, use is made intraperitoneally, orally, buccally, rectally, intramuscularly, subcutaneously or intravenously. In a further aspect of this embodiment, use is made in the form of tablets, sugar coated tablets (dragees), capsules, solutions, emulsions or suppositories. In a further aspect of this embodiment, use is made together with at least one other pharmaceutical substance. In a further aspect of this embodiment, the oral antidiabetic is selected from sulfonylureas, glinides, metformin, imidazolidinones, glitazones, α-glucosidase inhibitors, and dipeptylpeptidase IV inhibitors. In a further aspect of this embodiment, the person receiving prophylaxis and/or treatment is selected from: i) genetically predisposed persons with preceding diabetes-inducing diseases caused by viruses, said viruses selected from mumps viruses, coxsackie B viruses, rubella viruses, measles viruses, cytomegaloviruses, and influenza viruses, and/or ii) persons with at least one type 1 diabetic parent or sibling, and/or iii) persons with up-regulated diagnostic markers for inflammation of the pancreas. In a further aspect of this embodiment, the diagnostic marker is selected from glutamate decarboxylase (glutamic acid decarboxylase), tyrosine phosphatase IA-2, and islet cell antibodies (ICA).

In a further embodiment, an acetyl-11-keto-β-boswellic acid, 11-keto-β-boswellic acid, β-boswellic acid, acetyl-β-boswellic acid, 9,11-dehydro-β-boswellic acid, acetyl-9,11-dehydro-β-boswellic acid, α-boswellic acid, acetyl-α- boswellic acid, 11-dehydro-α-boswellic acid, acetyl-9,11-dehydro-α-boswellic acid, lupeolic acid, acetyl-lupeolic acid, 12-ursene-2-diketone, incensole, incensole acetate, a derivative, in particular an ester, a pharmaceutically acceptable salt thereof, a combination thereof, or a preparation containing one or more of these compounds is provided for the human medical or veterinary prophylaxis and/or treatment of a) damage to and/or inflammation of the islets of Langerhans and/or b) damage to the B-cells of the islets of Langerhans.

In one aspect of this embodiment, the damage to the islets of Langerhans and/or their B-cells is accompanied by inflammation (insulitis). In another aspect of this embodiment, the damage to and/or the inflammation of the islets of Langerhans and/or the damage to the B-cells of the islets of Langerhans is/are associated with type 1 diabetes, type 2 diabetes, or pancreatitis. In a further aspect of this embodiment, the type 1 diabetes is type 1a diabetes, LADA diabetes or type 1b diabetes. In a further aspect of this embodiment, the combination consists of acetyl-11-keto-β-boswellic acid and 11-keto-β-boswellic acid and/or pharmaceutically acceptable salts thereof. In a further aspect of this embodiment, acetyl-11-keto-β-boswellic acid and 11-keto-β-boswellic acid are contained in a preparation. In a further aspect of this embodiment, the use is made intraperitoneally, orally, buccally, rectally, intramuscularly, subcutaneously or intravenously. In a further aspect of this embodiment, the use is made in the form of tablets, sugar-coated tablets (dragees), capsules, solutions, emulsions or suppositories. In a further aspect of this embodiment, use is made together with at least one other pharmaceutical substance. In a further aspect of this embodiment, the pharmaceutical substance that is used is selected from antiphlogistics, oral antidiabetics, antioxidants, pentoxifylline, isoxazolene, interferons, gangliosides, α-adrenoceptor antagonists, nicotinamide, dimethylurea, lipid-lowering agents and herbal drugs. In a further aspect of this embodiment, the oral antidiabetic is selected from sulfonylureas, glinides, metformin, imidazolidinones, glitazones, α-glucosidase inhibitors, and dipeptylpeptidase IV inhibitors. In a further aspect of this embodiment, the person receiving the prophylaxis and/or the treatment is selected from: i) genetically predisposed persons with preceding diabetes-inducing diseases caused by viruses, said viruses selected from mumps viruses, coxsackie B viruses, rubella viruses, measles viruses, cytomegaloviruses, and influenza viruses, and/or ii) persons with at least one type 1 diabetic parent or sibling, and/or iii) persons with up-regulated diagnostic markers for inflammation of the pancreas. In a further aspect of this embodiment, the diagnostic marker is selected from glutamate decarboxylase, tyrosine phosphatase IV-2 and islet cell antibodies (ICA).

BRIEF DESCRIPTION OF THE DRAWINGS

Some of the embodiments described herein are explained in more detail by means of the following figures:

FIGS. 5A-C show the influence of a 5-, 10- and 21-day intraperitoneal administration of 150 mg/kg of a mixture of different boswellic acids obtained by an alcoholic extract from the oleogum resin of Boswellia serrata (BE) on the blood glucose level of mice treated with STZ (mean +/− SE; n=4-5).

FIGS. 9A-F show the influence of a 10-day intraperitoneal administration of 150 mg/kg of a mixture of different boswellic acids obtained by an alcoholic extract from the oleogum resin of Boswellia serrata (BE) on pro-inflammatory cytokines in the serum of mice treated with STC (C=untreated control; mean +/− SE; n=3-5).

DETAILED DESCRIPTION

Figure 1:
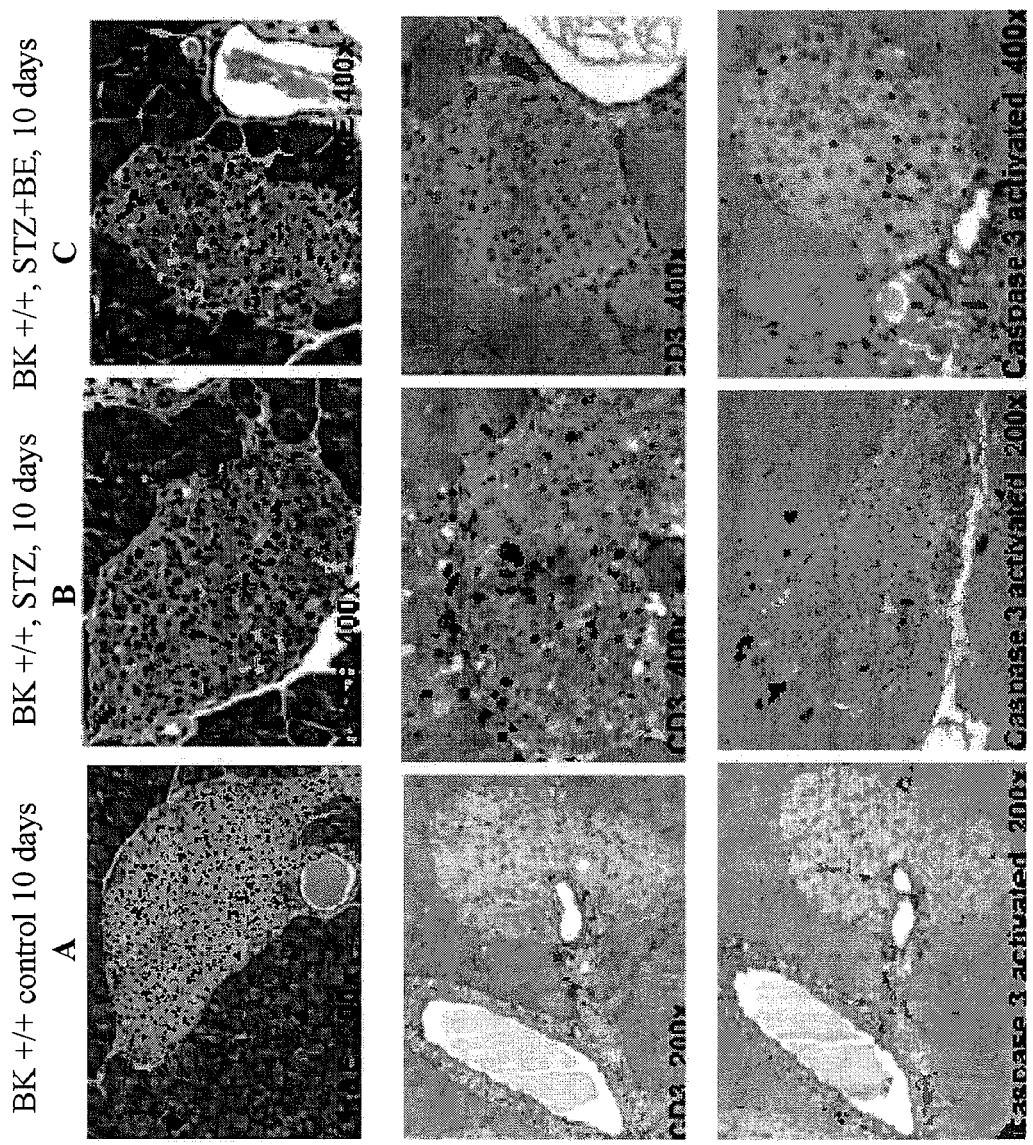
FIGS. 1A-C show the influence of a 10-day intraperitoneal administration of 150 mg/kg of a mixture of different boswellic acids obtained by an alcoholic extract from the oleogum resin of Boswellia serrata (BE) on the histologic image of the islets of Langerhans in mice treated with STZ (examination on the 10th day of treatment with BE; BK +/+ mouse strain used H&E, anti-CD3, and anti-activated caspase 3 staining; n=3-5).

Hence, there is a need for a causal treatment for damage and/or inflammation of the islets of Langerhans to causally treat or cure a diabetic condition. Furthermore, there is a need for an effective prophylaxis against damage and/or inflammation of the islets of Langerhans as well as against damage of the B-cells of the islets of Langerhans with the aim of preventing the cause of a diabetic condition. The therapeutic concept described herein is intended to be well tolerated without significant side effects. Furthermore, as described herein, treatment is possible before the onset of diabetes, or, in cases where diabetes has already occurred, treatment can prevent deterioration associated with further destruction of B cells.

It has been found that a mixture of boswellic acids or boswellic acids of a boswellic-acid containing preparation, as well as individual boswellic acids, can prevent damage and/or inflammation of the islets of Langerhans (insulitis) or can stop or reduce the same, and can prevent or cure damage, in particular inflammation-associated damage of B cells of the islets of Langerhans. The effect of the boswellic acids exhibits little side effects. The effect of the boswellic acids not only makes them suitable for treatment, but also for the prophylaxis of damage and/or inflammation of the islets of Langerhans, as well as of the B cells of the islets of Langerhans.

Embodiments described herein relate to the use of acetyl-11-keto-β-boswellic acid, 11-keto-β-boswellic acid, β-boswellic acid, acetyl-β-boswellic acid, 9,11-dehydro-β-boswellic acid, acetyl-9,11-dehydro-β-boswellic acid, α-boswellic acid, acetyl-α-boswellic acid, 11-dehydro-α-boswellic acid, acetyl-9,11-dehydro-α-boswellic acid, lupeolic acid, acetyl-lupeolic acid, 12-ursene-2-diketone, incensole, incensole acetate, a derivative, in particular an ester thereof, a physiologically tolerable salt thereof, a combination thereof, or a preparation containing one or more of these compounds for human medical or veterinary treatment and/or prophylaxis of: a) damage and/or inflammation of the islets of Langerhans and/or b) damage of the B-cells of the islets of Langerhans.

Embodiments described herein also relate to a method for human medical or veterinary treatment and/or prophylaxis of: a) damage and/or inflammation of the islets of Langerhans and/or b) damage of B-cells of the islets of Langerhans using a compound described herein.

The use or method according to the embodiments described herein relate to the treatment and/or the prophylaxis as described herein, wherein the damage of the islets of Langerhans and their B-cells can be accompanied by inflammation (insulitis). Frequently, the damage and/or inflammation of the islets of Langerhans and/or the B-cells of the islets of Langerhans are associated in patients with type 1 diabetes, type 2 diabetes, LADA type diabetes or pancreatitis.

In one embodiment, damage to the islets of Langerhans and/or the B-cells comprises damage to the morphologic structure as well as the physiological function. The extent of the damage can comprise all kinds and types of damage, e.g., from minor damage to very severe damage. Such damage is generally diagnosed by a malfunction of the islets of Langerhans, i.e., disturbed secretion of the hormones produced by the islets of Langerhans (e.g., insulin, glucagon, or somatostatin). Damage can also be detected by pancreas biopsy.

Boswellic acids are pentacyclic tri terpenes and form the main components of the resin of the Indian *Boswellia* tree (*Boswellia serrata*) and other *Boswellia* species (Ammon, HPT, Planta Med, 2006; 77: 1100-1116).

The effect of orally administered preparations made of the resin of different *Boswellia* species on the blood glucose level in alloxan-induced diabetes has been investigated. In the paper of Helal, Mostafa, Ashour and Kawash (2005) ("Effect of *Boswellia* Carterii Birdw. on Carbohydrate Metabolism in Diabetic Male Albino Rats", The Egyptian Journal of Hospital Medicine, 2005, Vol. 20: 38-45) experiments were carried out with alloxan-diabetic rats. Alloxan leads directly to the destruction of the insulin-producing B-cells by forming reactive oxygen species (ROS) In this study, only animals with a blood glucose level (BG) of at least 180-250 mg/dl were further examined. Due to the destruction of the B-cells, the animals were diabetic and were treated from that point on. They were dosed orally with an aqueous extract (not containing boswellic acids because they are not water-soluble) from the resin of *Boswellia carterii* for 30 days. Beside a reduction of the blood glucose level (BG), a normalization of the hypoinsulinemia and an increase in the glycogen in the animals treated with alloxan, upon histopathologic examination (H & E staining) the authors found a normal structure of the islets of Langerhans after treatment with aqueous *boswellia*" extract. These authors state that regeneration of the B-cells had taken place.

In a study by Helal and Abbas (2006) ("Effect of some herbal medicine on some biochemical parameters in diabetic rats", The Egyptian Journal of Hospital Medicine, 2006, Vol. 22: 98-110) rats were given a single dose of alloxan. After 48 hours the blood glucose level was measured. Again, only those rats with a blood glucose level higher than 250 mg/dl, i.e. which were clearly diabetic, were further examined. These animals were treated orally with an aqueous extract from *Boswellia carterii* for 30 days. In this study, the blood glucose levels decreased from 266.8 mg/dl to the reference values. The same effect as with the aqueous extract from *Boswellia carterii* was observed under the treatment with aqueous extracts from *Nigella sativa, Aloe vera, Ferula asa foetida* and *Commiphora myrrha*. With all these substances the insulin level in the blood increased.

The authors of the above-mentioned studies attribute the decrease of the blood glucose level with the increased insulin secretion, reduced insulin resistance and increased glycogen synthesis due to the aqueous extract-all a consequence of a stimulation of insulin secretion.

In a study by Kavitha et al. (2007) ("Hypoglycemic and other related effects of *Boswellia glabra* in Alloxan-induced diabetes rats", Indian J Physiol Pharmacol 2007; 51 (1): 29-39) diabetes was also induced by administering 200 mg/kg of Alloxan. Only animals with a blood glucose level above 300 mg/dl two days after treatment with Alloxan were studied further. Here, the oral administration of aqueous extracts of leaves and roots of *Boswellia glabra* was tested with respect to their effect on blood glucose, cholesterol, triglycerides, urea, creatinine in the blood and serum enzymes over a period of 28 days. The blood parameters improved. The authors of this study attribute this effect to a repair of damaged B-cells.

None of these studies, however, demonstrate the specific effect of boswellic acids for the use and/or treatment and for the prophylaxis of damage or insulitis or inflammation-induced damage to the B-cells of the islets of Langerhans. Furthermore, these studies do not contain any statement that the pathogenesis of diabetes can be prevented or ameliorated using the boswellic acids.

As described herein (e.g., using the "multiple low dose-Streptozotocin" (MLD-STZ) diabetes model, which is an acknowledged animal model for inducing diabetes that is associated with insulitis), damage/inflammation and apoptosis as well as the shrinking of the cells of the islets of Langerhans can be prevented, cured, or ameliorated with an extract of the resin from *Boswellia serrata* that contains a mixture of boswellic acids. Furthermore, by using this model, both the boswellic-acid containing extract and the 11-keto-β-boswellic-acid as well as the acetyl-11-keto-β-boswellic acid that are contained in this extract can reduce the increase of the pro-inflammatory cytokines and, thus, damage to/insulitis of the islets of Langerhans.

As described herein, boswellic acids, alone or in combination with each other, as well as preparations containing boswellic acids, can be used. Preferably, the following boswellic acids are used: acetyl-11-keto-β-boswellic acid, 11-keto-β-boswellic acid, β-boswellic acid, acetyl-β-boswellic acid, 9,11-dehydro-β-boswellic acid, acetyl-9,11-dehydro-β-boswellic acid, α-boswellic acid, acetyl-α- boswellic acid, 11-dehydro-α-boswellic acid, acetyl-9,11-dehydro-α-boswellic acid as well as lupeolic acid, acetyl-lupeolic acid, 12-ursene-2-diketone, incensole, incensole acetate. Furthermore, derivatives of these boswellic acids as well as physiologically tolerable salts thereof can be used. Such derivatives of boswellic acids include esters, e.g., methyl-, ethyl-, butyl-, allyl-esters as well as esters with other physiologically tolerable alcohols. Examples of physiologically tolerable salts of boswellic acids are Na, K, Mg or ammonium salts.

As one of skill in the art will recognize the term "physiologically tolerable" can generally be substituted with the term "pharmaceutically acceptable," e.g., when referring to salts of compounds.

As used herein, the terms "reduce," "ameliorate," "treat," and variants thereof can include, e.g., any reduction in the risk of developing a condition, prevention/prophylaxis of a condition, improvement of a condition, or reduction in the progression or severity of a condition.

Some examples of boswellic-acid containing preparations include herbal preparations, such as extracts from parts of plants, preferably from resins from the plant family of Burseraceae such as, for example, Boswellia carterii, Boswellia sacra, Boswellia frereana, Boswellia bhaudajiana, Boswellia papyfera, Boswellia neclecta, Boswellia odorata, Boswellia dalzielli, Boswellia serrata, among others. However, other boswellic acid-containing preparations that are pharmacologically and physiologically tolerable and that are prepared using known methods can be used.

In one embodiment, an extract of Boswellia serrata is used. The extract can be prepared from any part of boswellic acid-containing plants. Preferably, the extract is prepared from the resin of boswellic acid-containing plants. Preferably, the extract from the resin of Boswellia serrata is used. The extract can be prepared from the plant parts to be extracted in any known manner. Preferably, the extract is prepared by extraction using an organic solvent. The organic solvent is preferably selected from methanol, ethanol, chloroform, carbon tetrachloride, ethyl acetate, toluol, xylol, acetone, acetylacetone or dimethylformamide or mixtures of these solvents. It is particularly preferred to prepare the extract by methanolic extraction, e.g., prepared according to Singh et al. (G. B. Singh, Boswellic acids, Drugs of the Future, 1993, 18: 307-309).

According to a study by Buchele and Simmet (2003, J. Chromatogr. B; 791: 21-30), in incense extract the following pentacyclic triterpenes have been found in the following percentages:

| | |
|---|---|
| α-boswellic acid | 13.78% |
| acetyl-α-boswellic acid | 3.37% |
| lupeolic acid | 2.61% |
| acetyl lupeolic acid | 1.10% |
| 11-dehydro-α-boswellic acid | 0.18% |
| acetyl-9,11-dehydro-α-boswellic acid | 0.06% |
| β-boswellic acid | 19.20% |
| acetyl-β-boswellic acid | 10.04% |
| 11-keto-β-boswellic acid | 6.66% |
| acetyl-11-keto-β-boswellic acid | 3.81% |
| 9,11-dehydro-β-boswellic acid | 0.83% |
| acetyl-9,11-dehydro-β-boswellic acid | 0.52% |

In some embodiments, an extraction method is used in such a way that the compounds described herein are extracted from the boswellic acid-containing plant.

In some embodiments, boswellic acids or preparations containing the same, preferably herbal preparations, can be used alone or in combination with one or more additional pharmaceutical substances. Examples of pharmaceutical substances that can be combined with boswellic acids or with preparations containing the same are: aqueous extracts from plant parts of Boswellia species and other Burseraceae species, antiphlogistics, e.g. acetylsalicylic acid, diflunisal, indometacin, acemetacin, diclofenac, lonazolac, ibuprofen, dexibuprofen, flurbiprofen, ketoprofen, dexaketoprofen, naproxen, tiaprofen acid, piroxicam, meloxicam, lornoxicam, paracetamol, phenazon, propyphenazon, metamizol, insulin, oral antidiabetics such as, for example, sulfonylureas, glynides, metformin, imidazolidinone, glitazone, alpha-glucosidase inhibitors (acarbose), dipeptidylpeptidase IV (DPP IV) inhibitors, cyclosporin A, antioxidants, pentoxyphylline, isoxazoles, interferons, gangliosides, alpha-adrenozeptorant agonists, nicotinamide, dimethylurea. Furthermore, the boswellic acids or preparations containing boswellic acids can also be combined with additional preparations made from plants that have a hypoglycaemic or hypolipidaemic effect, as well as with statins, fibrates, nicotinic acid derivatives, ion exchangers etc. Preferred examples of hypoglycaemically active plants are Pterocarpus marsurpium, Stevia rebaudiana, and Momordica charantia.

In some embodiments, oral, buccal, rectal, subcutaneous, intravenous or intraperitoneal administration is used. For example, the boswellic acids or the preparations containing the same can be formulated by a known method that is suitable for the form of administration concerned. Examples of corresponding pharmaceutical dosage forms are tablets, powders, granulates, sugar-coated tablets (dragees), capsules, solutions, emulsions, or suppositories.

The dosage of the substances described herein, or the preparations concerning these substances, depends on the extract preparation selected, the boswellic acids selected, the severity of the condition as well as on the relation of body surface to body weight of the individual to be treated. The exact dosage can be ascertained by a physician in a suitable way. A suitable standard dosage, for example, is the administration of about 400 to about 500 mg of extract three times a day (for example the product H15 of the company Gufic Ltd. Mumbai). A suitable dosage of 11-keto-β-boswellic acid for humans can range from about 0.2 mg/kg to about 4.0 mg/kg, preferably from about 0.4 mg /kg to about 8.0 mg/kg, three times a day. A suitable dosage of acetyl-11-keto-β-boswellic acid for humans can range from about 0.2 mg/kg to about 4.0 mg/kg, preferably from about 0.5 mg/kg to about 10.0 mg/kg, three times a day A particularly preferred dosage is about 1 mg/kg body weight for 11-keto-β-boswellic acid and about 2 mg/kg body weight for acetyl-11-keto-β-boswellic acid. These dosages refer to oral administration. In a therapy over a longer period of time, due to the long half life of boswellic acids, an accumulation of boswellic acid in the blood over the time may occur. Effective concentrations may therefore accumulate in the blood after a longer period of time. Preferably, boswellic acids or boswellic acid-containing preparations are administered together with a meal, and are thus better resorbed.

The uses described herein are particularly suited for the treatment and/or prophylaxis of damage to the islets of Langerhans and/or damage to the B-cells of the islets of Langerhans. Frequently, the damage to the islets of Langerhans and/or to their B-cells is accompanied by inflammation (insulitis). The inflammation or the inflammation-induced damage can occur without diabetes or can be associated with type 1 diabetes, type 2 diabetes or pancreatitis. Examples for type 1 diabetes are type 1A diabetes, LADA diabetes and type 1B diabetes.

The uses described herein maybe suited for the following groups of persons:
  i) persons with a genetic predisposition for type 1 diabetes with preceding diabetes-inducing diseases, e.g. diseases caused by viruses, such as mumps viruses, COX viruses, rubella viruses, measles viruses, cytomegaloviruses, or influenza viruses, and/or
  ii) persons, among whose first-degree relatives, e.g. parents or siblings, type 1 diabetes has occurred, or
  iii) persons having up-regulated diagnostic markers for the development of diabetes. Such diagnostic markers include glutamate decarboxylase (GAD), tyrosine phosphatase IA2, and islet cell antibodies (ICA).

Frequently, diabetes, in particular type 1 diabetes, is associated with insulitis.

In LADA diabetes and in a number of type 2 diabetic persons, onset of insulitis occurs later. As a consequence to damage, frequently accompanied/followed by inflammation, B-cells are damaged and/or destroyed, which results in an increase of the blood glucose level.

The embodiments described herein generally were found to have few side effects. In some embodiments, side effects that arise can include epigastric pain, hyperacidity and nausea.

Some embodiments relate to the therapeutic and/or prophylactic treatment of damage of the islets of Langerhans and/or damage of the B-cells of the islets of Langerhans, wherein the damage of the islets of Langerhans and/or their B-cells is preferably accompanied by inflammation (insulitis). The above statements concerning the uses described herein apply accordingly.

EXAMPLES

The following examples are intended to further illustrate the subject matter described herein.

Example 1 (Reference Example)

Effect of Acetyl-11-keto-β-boswellic Acid (AKBA) on Inflammation Parameters in Human Type 1 Diabetes and MLD-STZ Induced Diabetes in Rodents (Mouse, Rat)

In invitro experiments with mouse splenocytes, monocytes, human thrombocytes and PML, the effect of acetyl-11-keto-β-boswellic acid on typical inflammation markers was tested. The experiments were carried out according to the review of HPT Ammon, "Boswellic acids in chronic inflammatory diseases", Planta Medica 2006, 72: 1100-1116.

According to technical literature, the following parameters are increased in splenocytes and PBMC in human type-1 diabetes: IFN-γ, IL-2, TNF-α, IL-1β, NF-κB. In MLD-STZ diabetes, the following inflammation parameters in lymph node cells and peritoneal macrophages are increased: IFN-γ, IL-2, TNF-α. Beyond that, an influx of macrophages into the pancreatic islets is observed.

The results of the effects of AKBA on inflammation parameters as described in technical literature are contained in Table 1.

TABLE 1

| Effect of AKBA on Inflammation Markers | |
|---|---|
| 5-Lipoxygenase (leukotriene) | Lowered |
| Cyclooxygenase 1 (prostaglandin) | Lowered |
| IL-1β | Lowered |
| IL-2 | Lowered |
| IFN-γ | Lowered |
| TNF-α | Lowered |
| NF$_K$B | Lowered |
| C3-Convertase | Lowered |
| Elastase | Lowered |

Consequently, it has been found that with acetyl-11-keto-β-boswellic acid, a reduction of the relevant inflammation parameters can be achieved in vitro.

Example 2

The Effect of a Mixture of a Boswellic-acids Containing Extract From the Oleogum Resin of *Boswellia serrata* (BE) on Streptozotocin Diabetes A methanolic extract from *Boswellia serrata* (BE) was investigated in accordance with the methods described in G. B. Singh, Boswellic acids, Drugs of the Future, 1993, 18: 307-309. The boswellic acids identified were β-boswellic acid, acetyl-β-boswellic acid, 11-keto-β-boswellic acid, acetyl-11-keto-β-boswellic acid.

The use of "multiple low dose streptozotocin" (MOL-STZ diabetes) is an acknowledged animal model for inducing diabetes that occurs frequently in association with insulitis, which corresponds to IDDM in humans. In the pathogenesis, macrophages and T-lymphocytes infiltrate the islets of Langerhans and the B-cells are destroyed. MLD-STZ induced diabetes is very well suited for investigating the anti-diabetic and/or anti-inflammatory effect of drugs on the pancreatic islets. For inducing MLD-STZ diabetes, a mouse is dosed with 40 mg/kg STZ per day intraperitoneally (i.p.) over 5 days. During this time there is no B-cell destruction. Only after 10 to 15 days after the first injection of STZ do signs of inflammation of the islets of Langerhans appear, when T-lymphocytes infiltrate and the B-cells are being destroyed. After about 16 days, the symptoms of the inflammation have disappeared again. Most B-cells have died. As a consequence, insulin secretion is reduced or no longer existent (cf. McEvoy et al. 1984, "Multiple low-dose streptozotocin-induced diabetes in the mouse", Evidence for stimulation of a cytotoxic cellular immune response against an insulin-producing beta cell line, J Clin Invest, 74:715-22). This animal model of experimental induction of diabetes mellitus essentially corresponds with the pathogenesis of type 1 diabetes in young humans.

In order to investigate the effect of an extract containing boswellic acids on the damage and/or inflammation of the islets of Langerhans, a group of mice was dosed with streptozotocin alone and another group of mice was dosed with streptozotocin plus boswellic acid extract (a mixture of boswellic acids with an overall concentration of all boswellic acids of 62%) The aforesaid extract contained 5.51% KBA and 4.96% AKBA. From the 1st to the 10th day, C3M/HeN and Bk +/+ were administered i.p with a dose of 150 mg/kg body weight in male mice of strains bred in the laboratory.

FIG. 1 shows histologic sections through a mouse pancreas 10 days after treatment with streptozotocin or streptozotocin plus boswellic acid extract. H&E staining was used for immunohistochemical detection of CD3-receptor complexes (to show the presence of T-lymphocytes as inflammation markers), as well as an immunohistochemical detection of the activated caspase 3 enzyme (as marker for the existence of apoptosis).

The left column (FIG. 1A) shows histological sections of pancreata of control mice with normal morphology in the endocrine region of the pancreas without inflammation (normal H & E staining, no T-lymphocytes and no signs of apoptosis).

The middle column (FIG. 1B) shows histological sections of pancreata of mice 10 days after treatment with streptozotocin. Inflammation in the endocrine region of the pancreas (H & E staining and detection of CD3 receptor complexes of T-lymphocytes) is shown. Moreover, apoptosis could be observed (caspase 3 is activated).

The right column (FIG. 1C) shows histological sections of pancreata of mice that were treated with streptozotocin and boswellic extract. Here, no signs of inflammation, neither with H & E staining nor in immunohistochemical detection of T-lymphocytes, could be found. Furthermore, no signs of apoptosis of cells were detected (there is no activated caspase 3).

These immunohistochemical results show that the administration of the *boswellia* extract both prevents the damage and the inflammation of the islets of Langerhans caused by STZ as well as the apoptosis of cells.

Figure 2:
FIGS. 2A-B show the influence of a 10-day intraperitoneal administration of 150 mg/kg of a mixture of different boswellic acids obtained by an alcoholic extract from the oleogum resin of Boswellia serrata (BE) on the histologic image of the islets of Langerhans in mice treated with STZ (examination 35 days after the first administration of BE; BK +/+ mouse strain used; H&E staining; n=3-5).
Figure 2:

In FIG. 2, histological sections from a mouse pancreas 35 days after the treatment with streptozotocin and *boswellia* extract (FIG. 2B) or streptozotocin alone (FIG. 2A) are shown. Different sizes of the islets of Langerhans were seen with the same magnification applied. Animals that were only treated with streptozotocin show shrinked endocrine regions in comparison to animals treated with streptozotocin and *boswellia* extract (H&E staining, 40-fold magnification). This indicates that streptozotocin alone in connection with damage/inflammation (cf. FIG. 1) led to shrinking of the islets of Langerhans, this shrinking occurring as a consequence of a massive death of B-cells. This was not the case when, additionally, a mixture of boswellic acids was administered. The results shown in FIGS. 1 and 2 show that an extract from the resin of *Boswellia serrata* that contained a mixture of Boswellic acids prevented inflammation, the death of B-cells as well as the shrinking of the cells of the islets of Langerhans. This suggests that due to the death of B-cells, insulin production/secretion is considerably restricted in animals that have only been treated with STZ, whereas this is not the case with respect to animals that have been treated at the same time with *Boswellia* extract. The tests of blood glucose levels provide compelling evidence for this.

Figure 3:
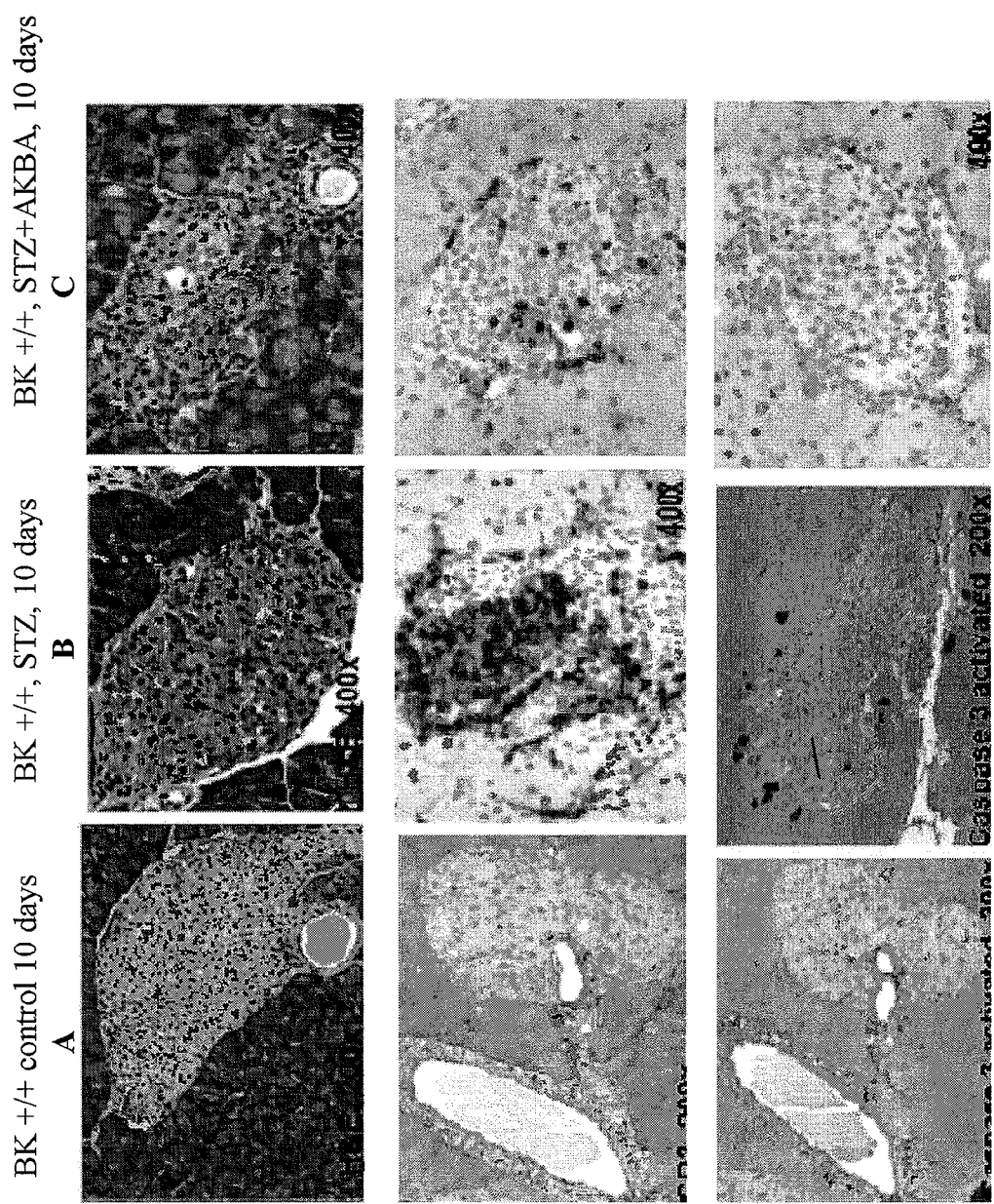
FIGS. 3A-C show the influence of a 10-day intraperitoneal administration of 15.0 mg/kg AKBA on the histologic image of the islets of Langerhans in mice treated with STZ. Examination on the 10th day of treatment with AKBA (BK +/+: mouse strain used; staining as in FIG. 1; n=4).
Figure 4:
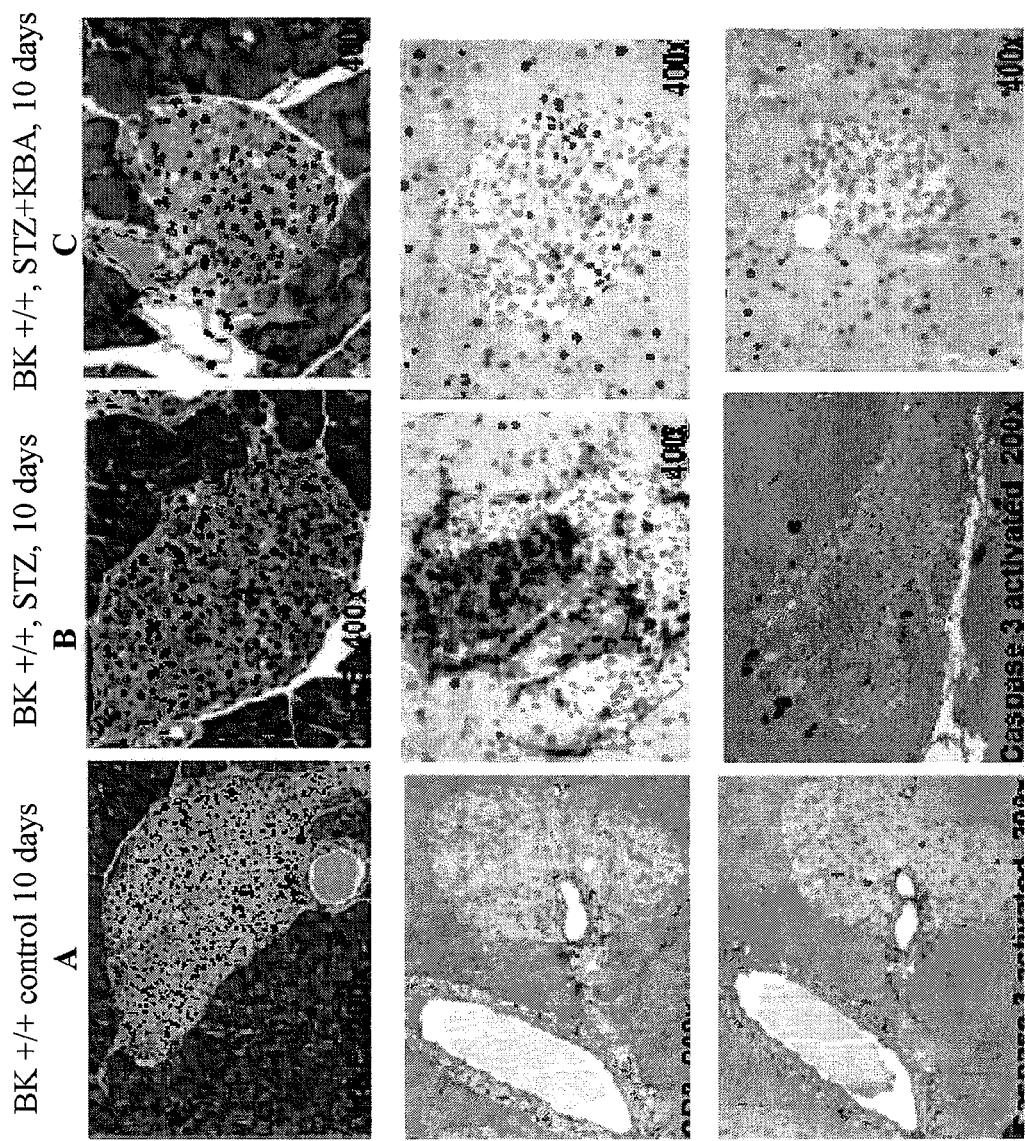
FIGS. 4A-C show the influence of a 10-day intraperitoneal administration of 7.5 mg/kg KBA on the histologic image of the islets of Langerhans in mice treated with STZ (examination on the 10th day of treatment with KBA; BK +/+: mouse strain used; staining as in FIG. 1; n=3).

In FIGS. 3 and 4, histological sections of mouse pancreas 10 days after the treatment with streptozotocin or streptozotocin plus AKBA (15 mg/kg, FIG. 2) or KBA (7.5 mg/kg, FIG. 3) is shown. The staining and the immunohistochemical detection were carried out as described for FIG. 1.

As in FIG. 1, the left columns (FIGS. 3A and 4A) show histological sections of control animals with normal morphology in the endocrine region of the pancreas without inflammation (normal H&E staining, no T-lymphocytes and no signs of apoptosis).

The middle columns (FIGS. 3B and 4B) show histological pancreas sections 10 days after treatment with streptozotocin. Here, inflammation, T-lymphocytes and apoptosis have been observed as well (cf. FIG. 1). The right columns (FIGS. 3C and 4C) show histological pancreas sections of mice that have been treated with streptozotocin plus AKBA or streptozotocin plus KBA. Here, after treatment with AKBA, no signs of inflammation and only minor signs of apoptosis were found. In the case of simultaneous treatment with STZ plus KBA, neither signs of inflammation nor signs of apoptosis were observed.

These immunohistochemical results show that, beside *Boswellia* extract, two of its boswellic acids (AKBA and KBA) can also prevent both an STZ-induced damage and inflammation of the islet of Langerhans and the apoptosis of cells.

FIG. 5 shows the effect of *Boswellia* extract (BE) on the blood glucose level of MLD-STZ diabetic mice in relation to the duration of the BE treatment.

Figure 5A:
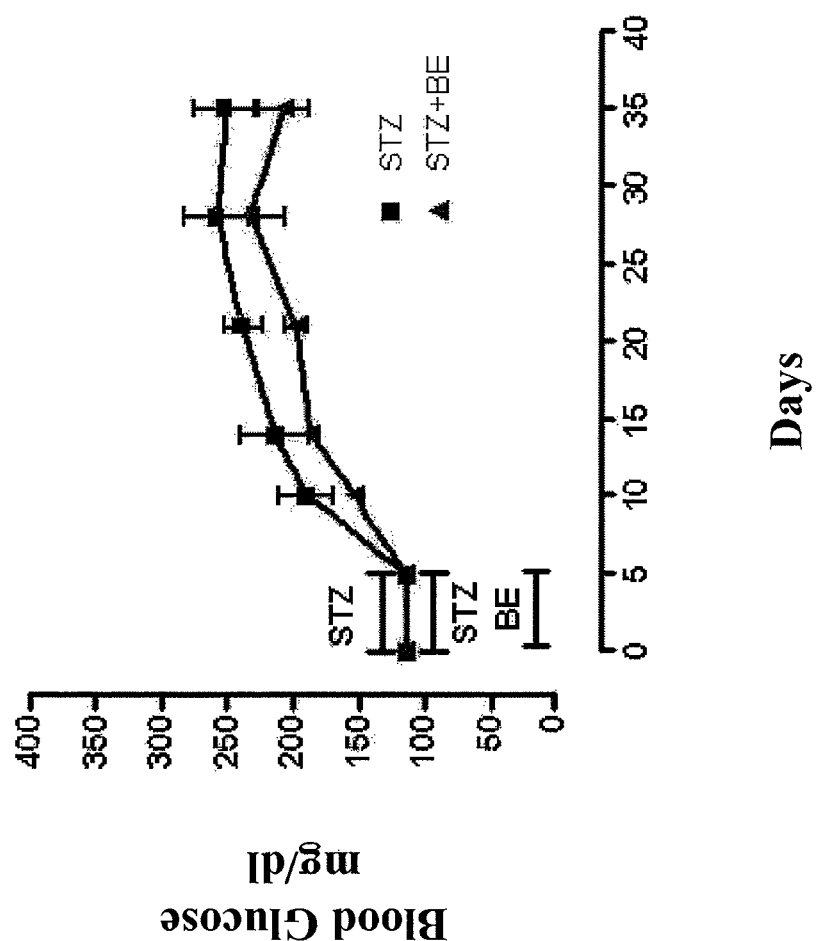
Figure 5B:
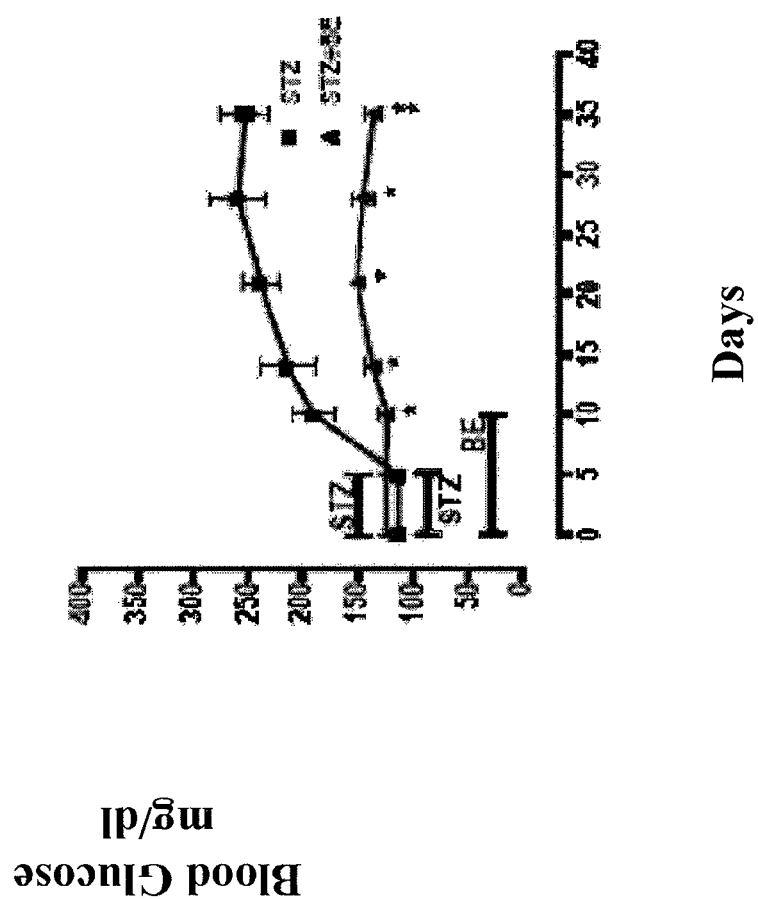

For inducing MLD-STZ diabetes, the animals were injected i.p. 40 mg/kg STZ a day for a period of five days. In group A the animals were additionally treated with 150 mg/kg BE i.p. for 5 days (FIG. 5A), in group B for 10 days (FIG. 5B) and in group C for 21 days (FIG. 5C).

In all three groups of the STZ-treated animals, no increase of the blood glucose level was observed after 5 days. An increase could only be observed after 10 days, wherein the increase continued.

A treatment with BE lasting only 5 days (group A) only slightly reduced the STZ-induced increase of the blood glucose level. With BE treatment over 10 days, however, the increase of the blood glucose level was remarkably weaker. The blood glucose level was around the normal value (group B).

Group B clearly shows that the blood glucose did not significantly increase further even after the BE treatment was discontinued. Similar results have been shown by group C.

These measurements show that, beside damage to B-cells and inflammation, BE has also prevented an increase in blood glucose with the effect that the insulin-producing B-cells mainly continue to be functional. Interestingly, after treatment with BE was discontinued, the blood glucose did not increase further. This shows that the BE prevented another onset of the disease.

We also ruled out that neither the extract nor the solvent Tween 80 had a direct impact on the blood glucose level.

Figure 6A:
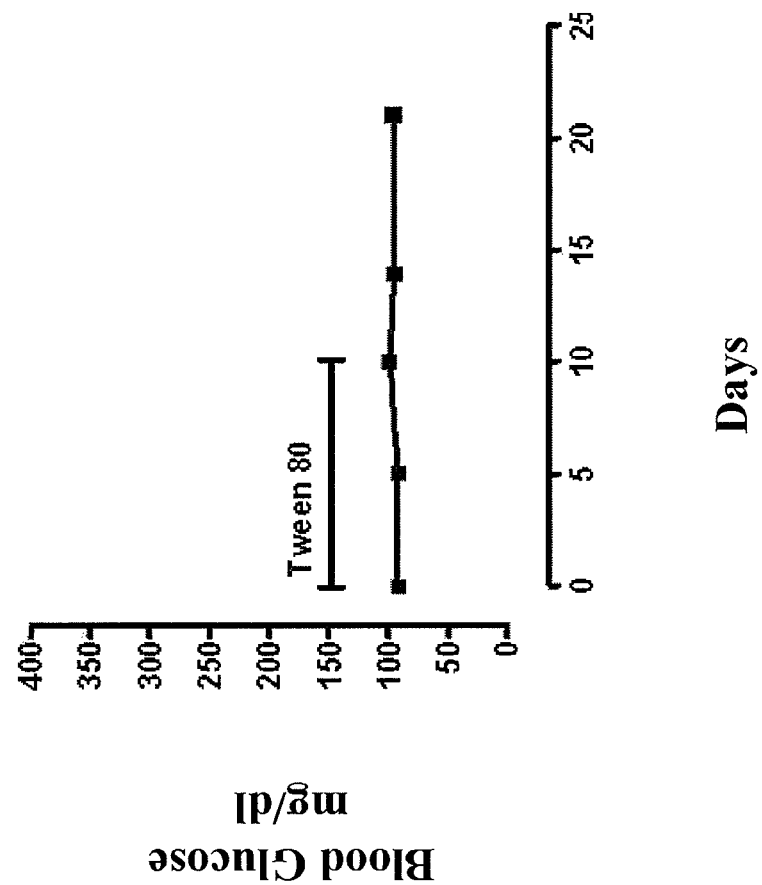
FIGS. 6A-B show the influence of a 7-day peritoneal administration of 150 mg/kg of a mixture consisting of different boswellic acids obtained by an alcoholic extract from the oleogum resin of Boswellia serrata (BE) as well as of the solvent Tween 80 on the blood glucose level of mice that were not treated with STZ (normal control; mean +/− SE; n=3).
Figure 6B:
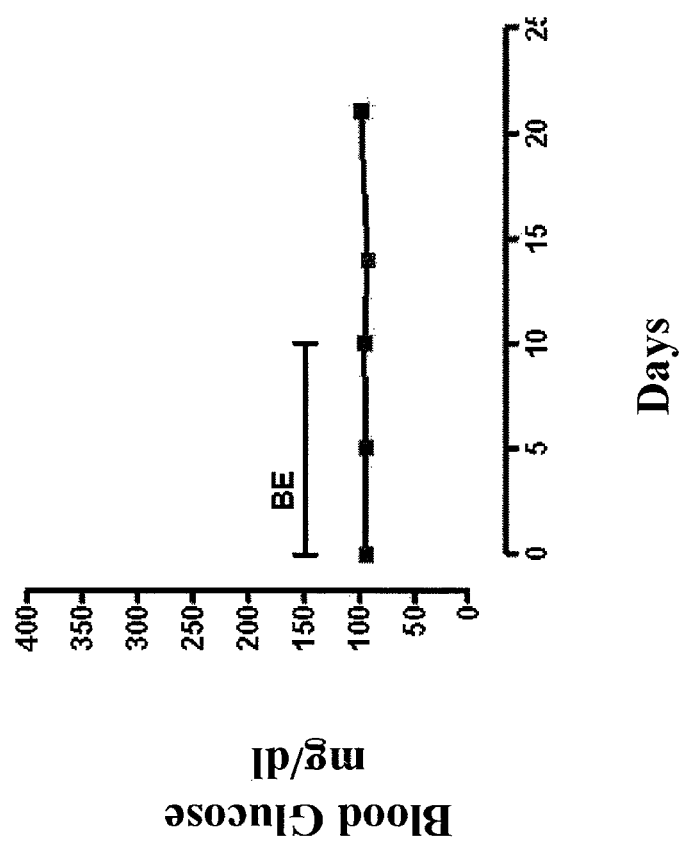

FIG. 6 shows the impact of the solubilizer for the extract, Tween 80 (CAS No. 9005-65-6), as well as the impact of the extract that is dissolved in this solubilizer on the blood glucose in normal mice that have not been treated with STZ. The animals were injected i.p. with (A) 0.1 ml/kg Tween 80 (1%) (FIG. 6A) or (B) 150 mg/kg BE over 7 days (FIG. 6B). In both cases no change in the blood glucose level was found. This shows that neither the solvent alone nor the BE dissolved in solvent have a direct impact on the blood glucose level of the mouse.

According to Btichele et al. 2003 ("Analysis of pentacyclic triterpenic acids from Frankincense gum resins and related phytopharmaceuticals by high-performance liquid chromatography. Identification of lupeolic acid, a novel pentacyclic triterpene", J. Chromatogr. B, 791: 21-30), it was shown that an alcoholic extract from the resin of *Boswellia serrata* contains a total of about 62% boswellic acids including acetylated and non-acetylated alpha and beta boswellic acids.

Of special interest among the Boswellic acids are acetyl-11-keto-β-boswellic acid (AKBA) and 11-keto-β-boswellic acid (KBA). Therefore, whether these two boswellic acids used individually can reduce an increase in the blood glucose level in MLD-STZ treated mice was investigated. The extract used according to the methods described herein contained 4.96% AKBA and 5.51% KBA.

Figure 7:
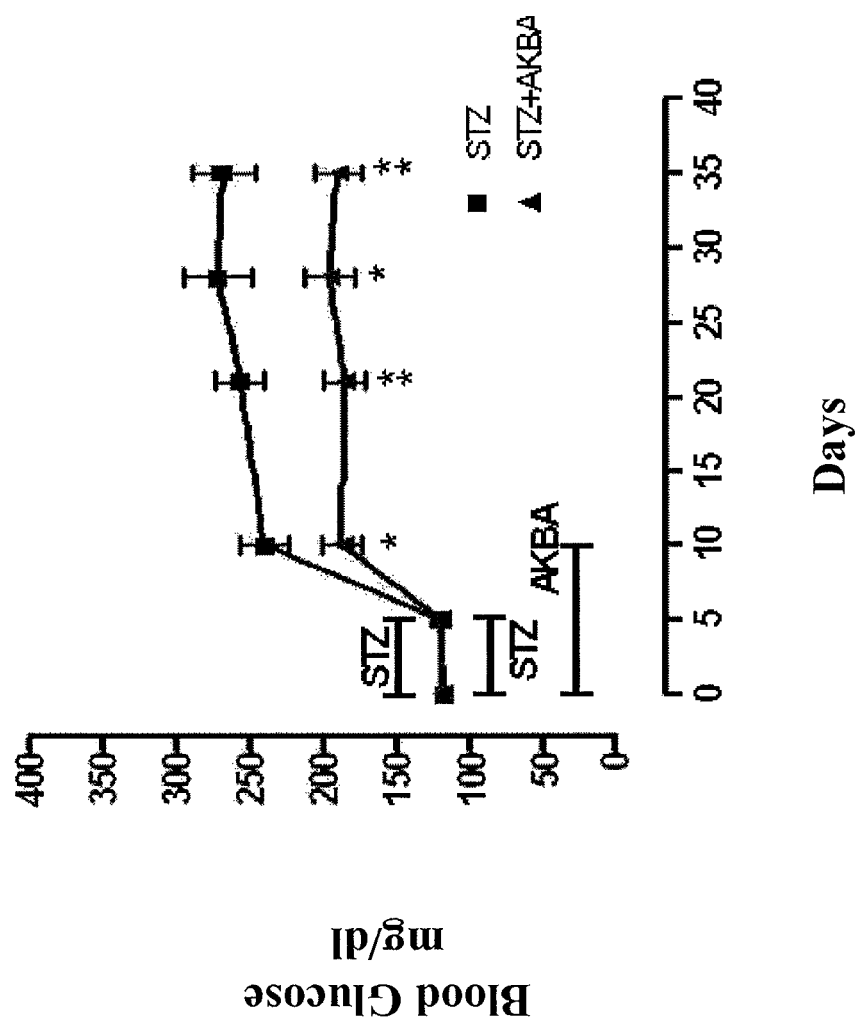
FIG. 7 shows the influence of a 10-day intraperitoneal administration of 7.5 mg/kg of 11-keto-β-boswellic acid (AKBA) on the blood glucose level of mice treated with STZ (mean +/− SE; n=4).

The effect of 15 mg/kg AKBA as a single substance on the blood glucose level in MLD-STZ diabetic mice is shown in FIG. 7. The animals were treated for 5 days with STZ as described above. AKBA in solution in Tween 80 was injected i.p. daily for 10 days. As is shown by FIG. 5, upon the administration of 15 mg/kg AKBA a significant reduction of the STZ-induced increase of the blood glucose level was observed.

After AKBA administration was discontinued after 10 days, no significant further increase of the blood glucose level was observed.

Figure 8:
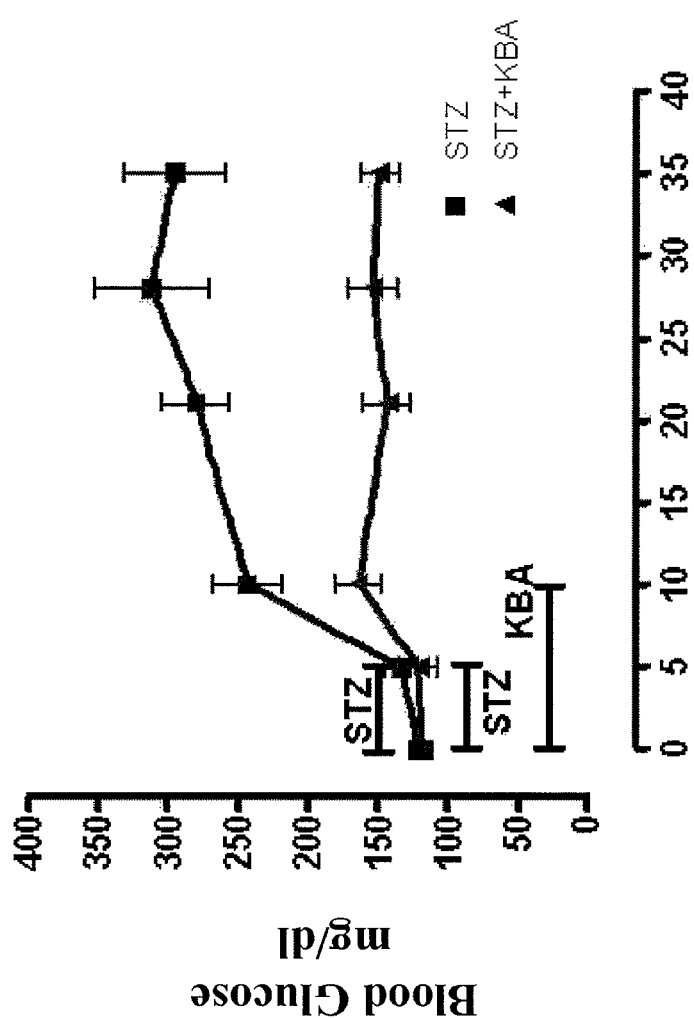
FIG. 8 shows the influence of a 10-day intraperitoneal administration of 15.0 mg/kg acetyl-11-keto-β-boswellic acid (AKBA) on the blood glucose level of mice treated with STC (mean +/− SE; n=4).
Figure 9A:
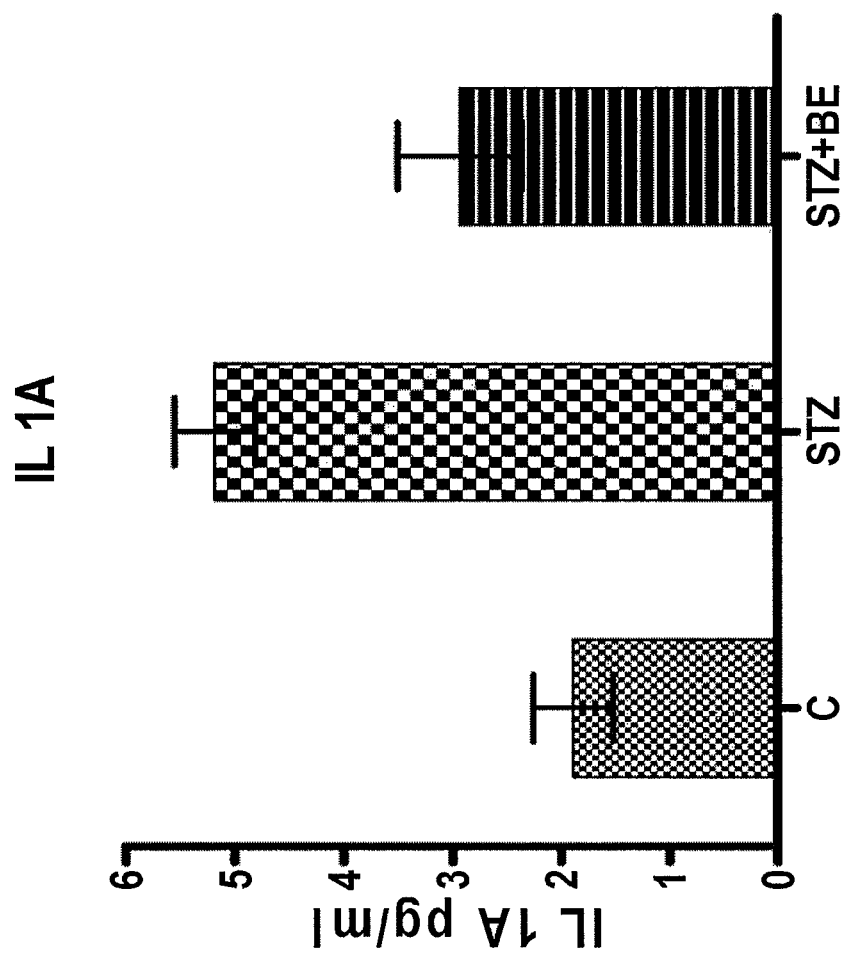
Figure 9D:
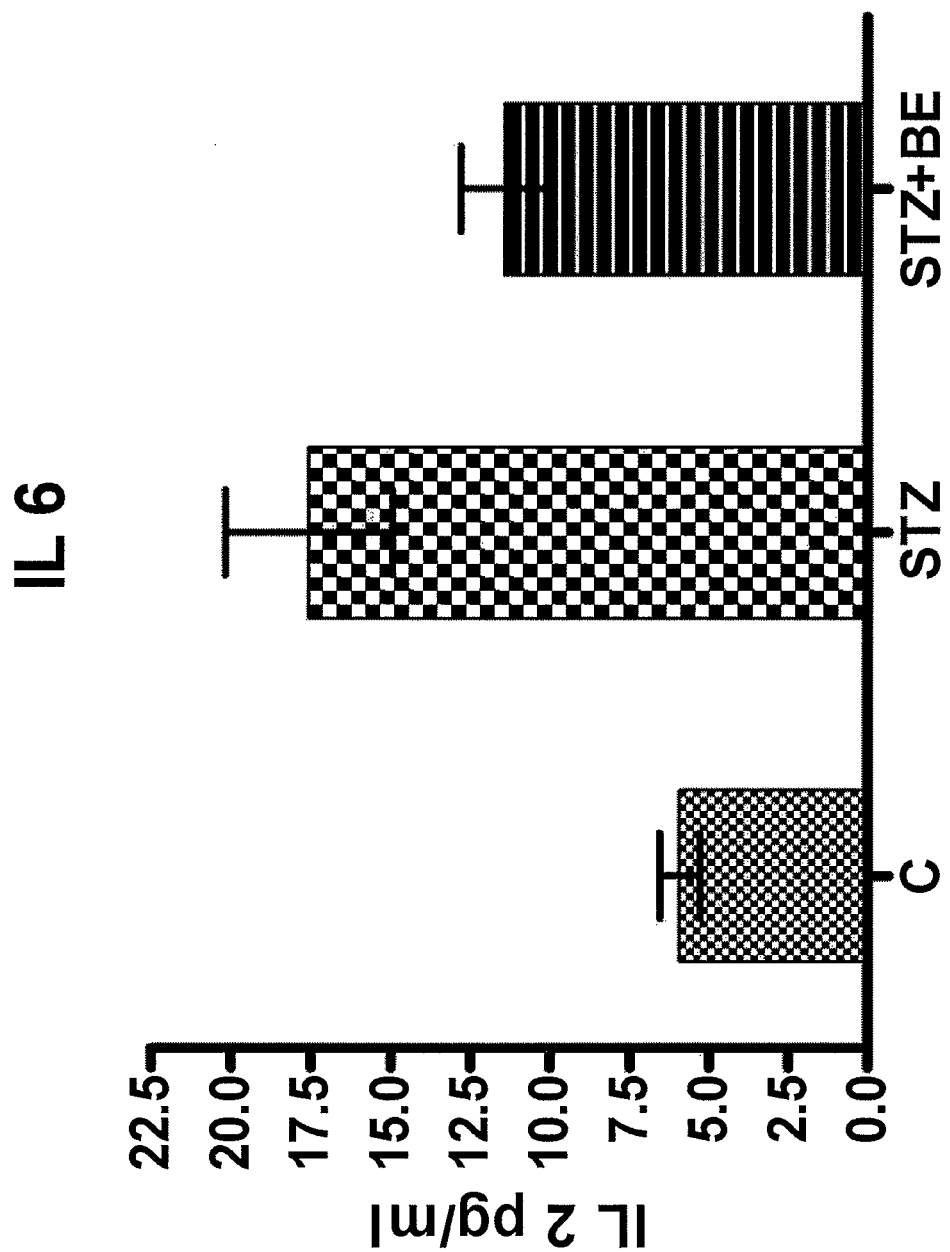
Figure 9E:
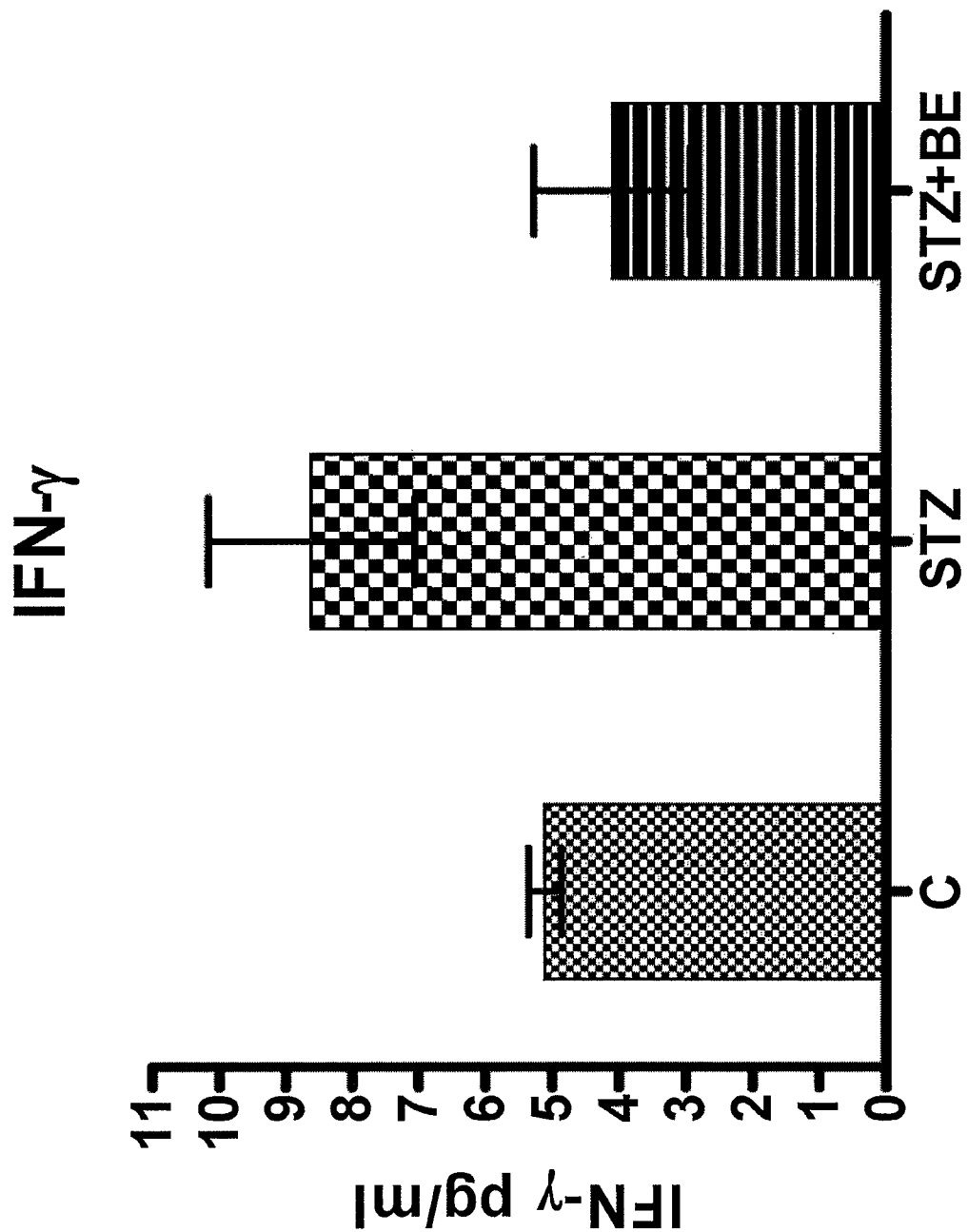
Figure 9F:
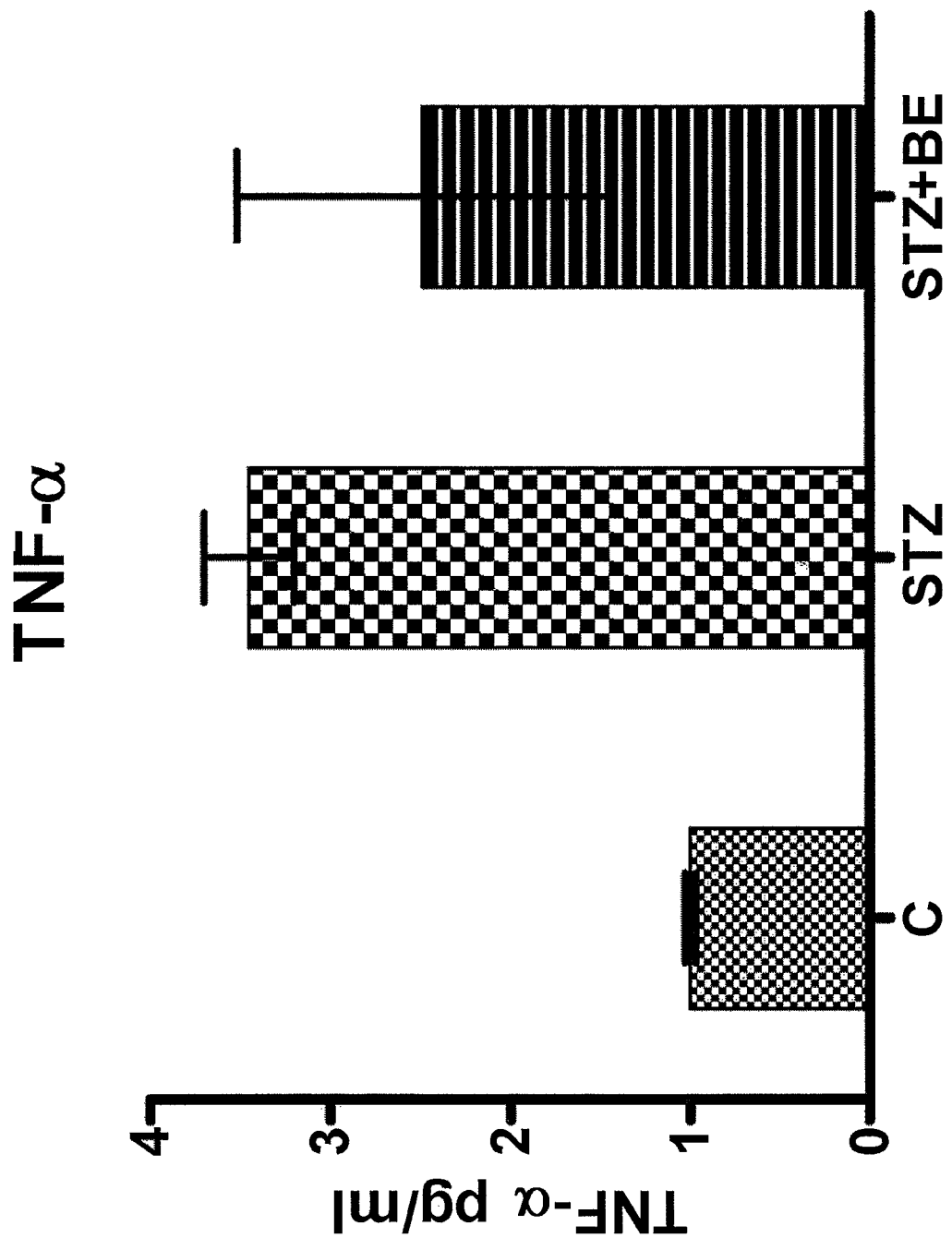
Figure 10A:
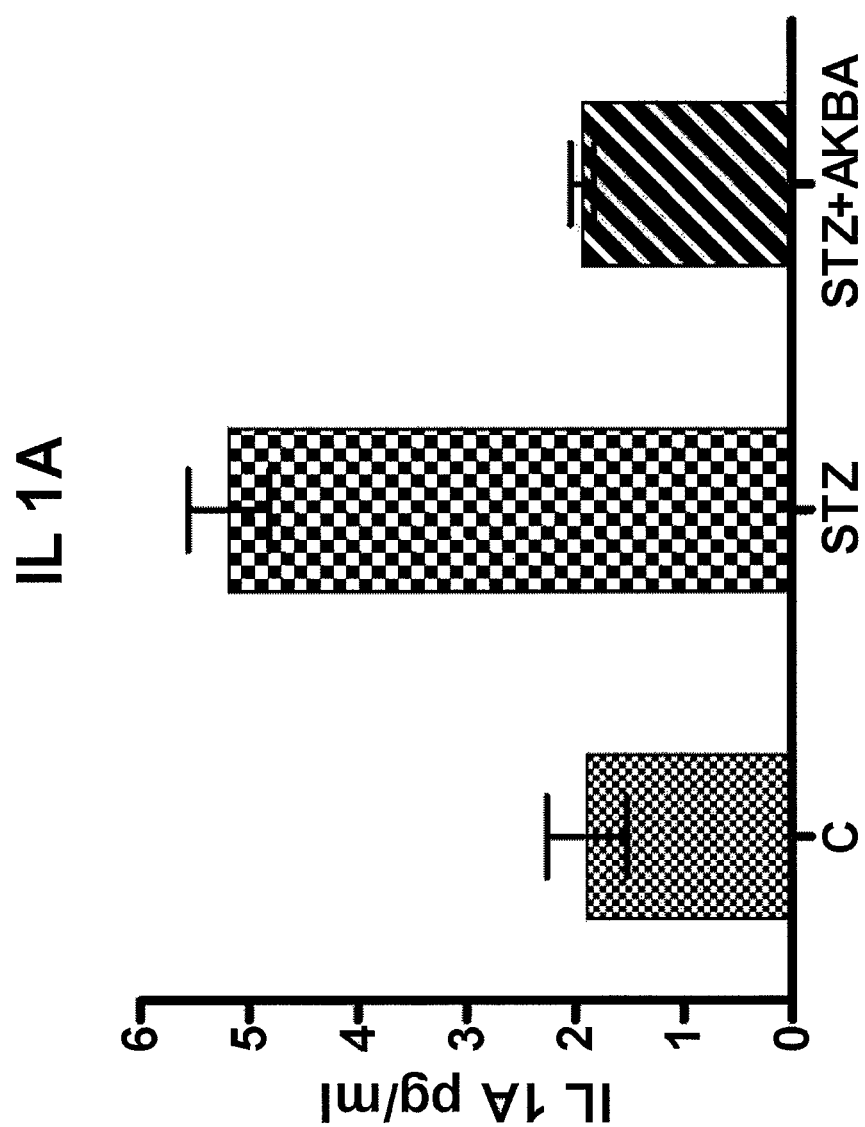
FIGS. 10A-F show the influence of a 10-day intraperitoneal administration of 15.0 mg/kg acetyl-11-keto-β-boswellic acid (AKBA) on pro-inflammatory enzymes in the serum of STC-treated mice (C=untreated control group; mean +/− SE; n=3).
Figure 10B:
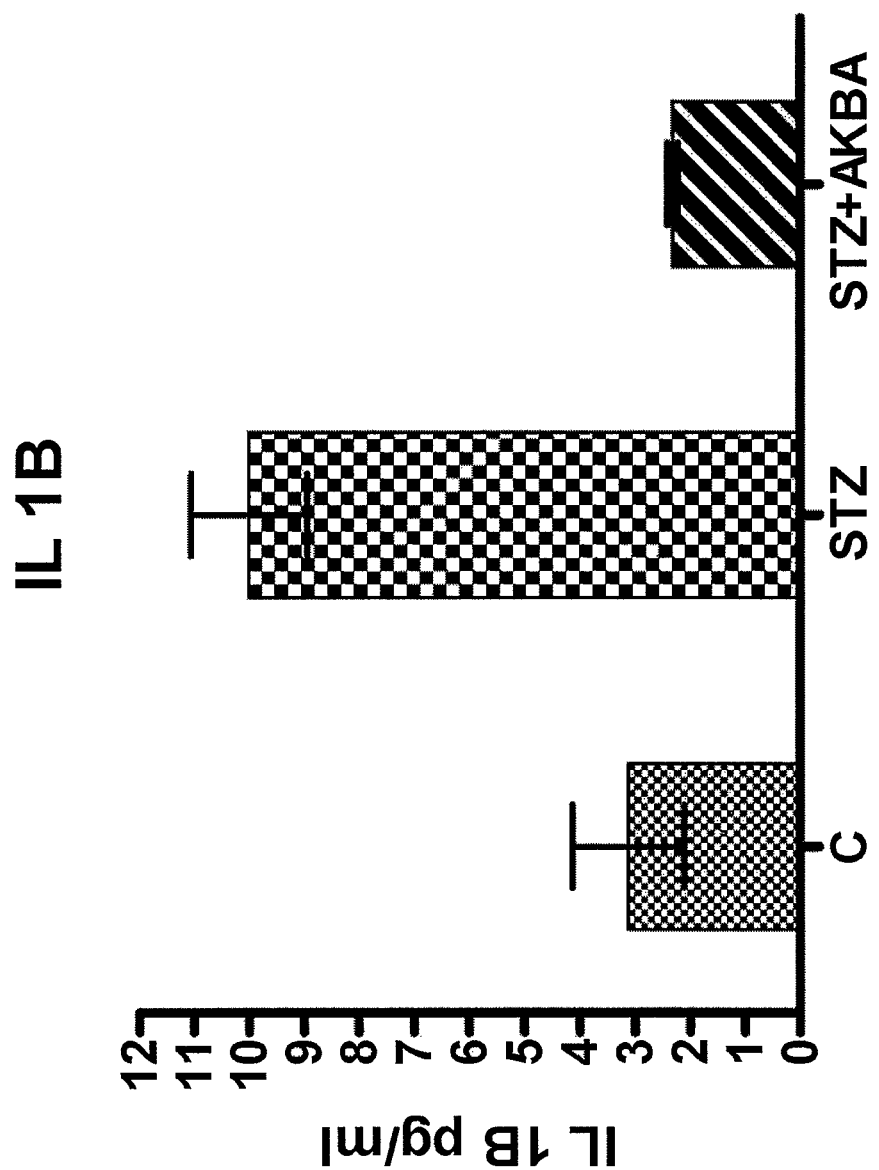
Figure 10C:
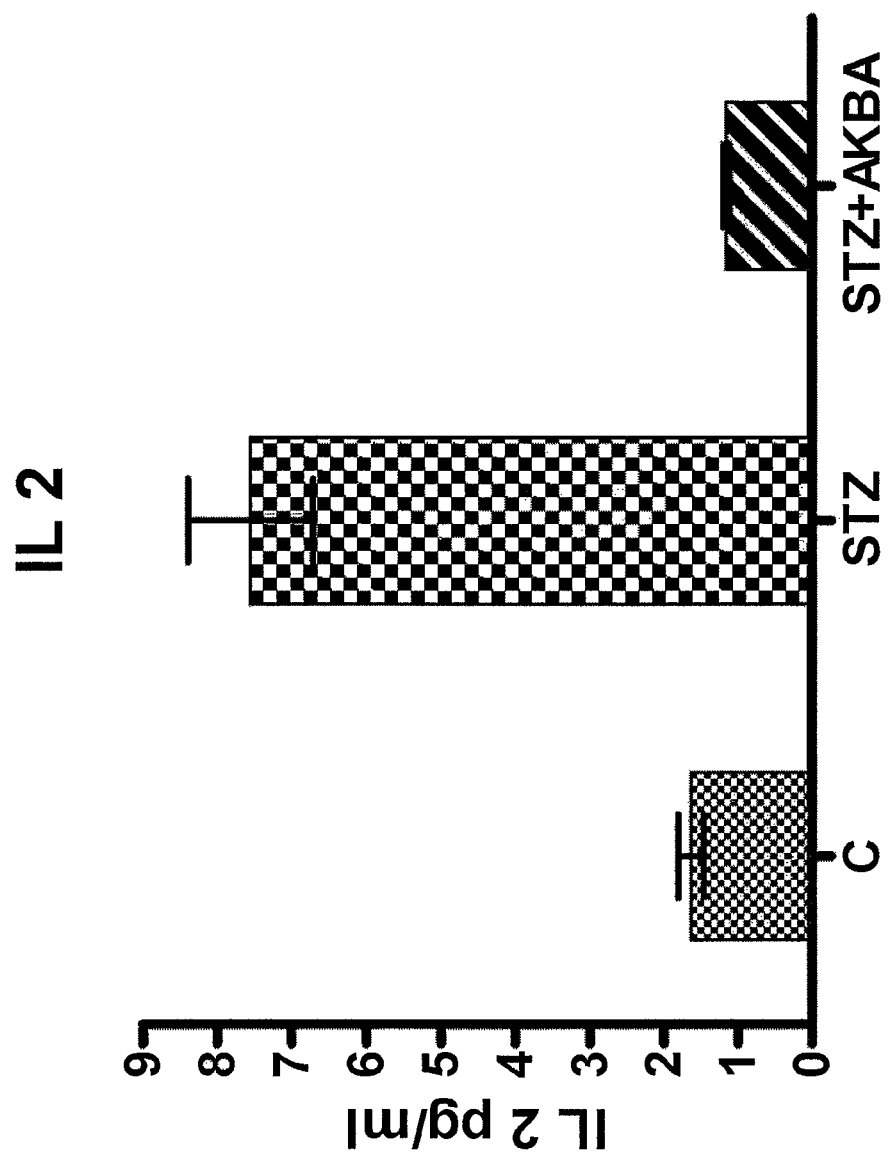
Figure 10D:
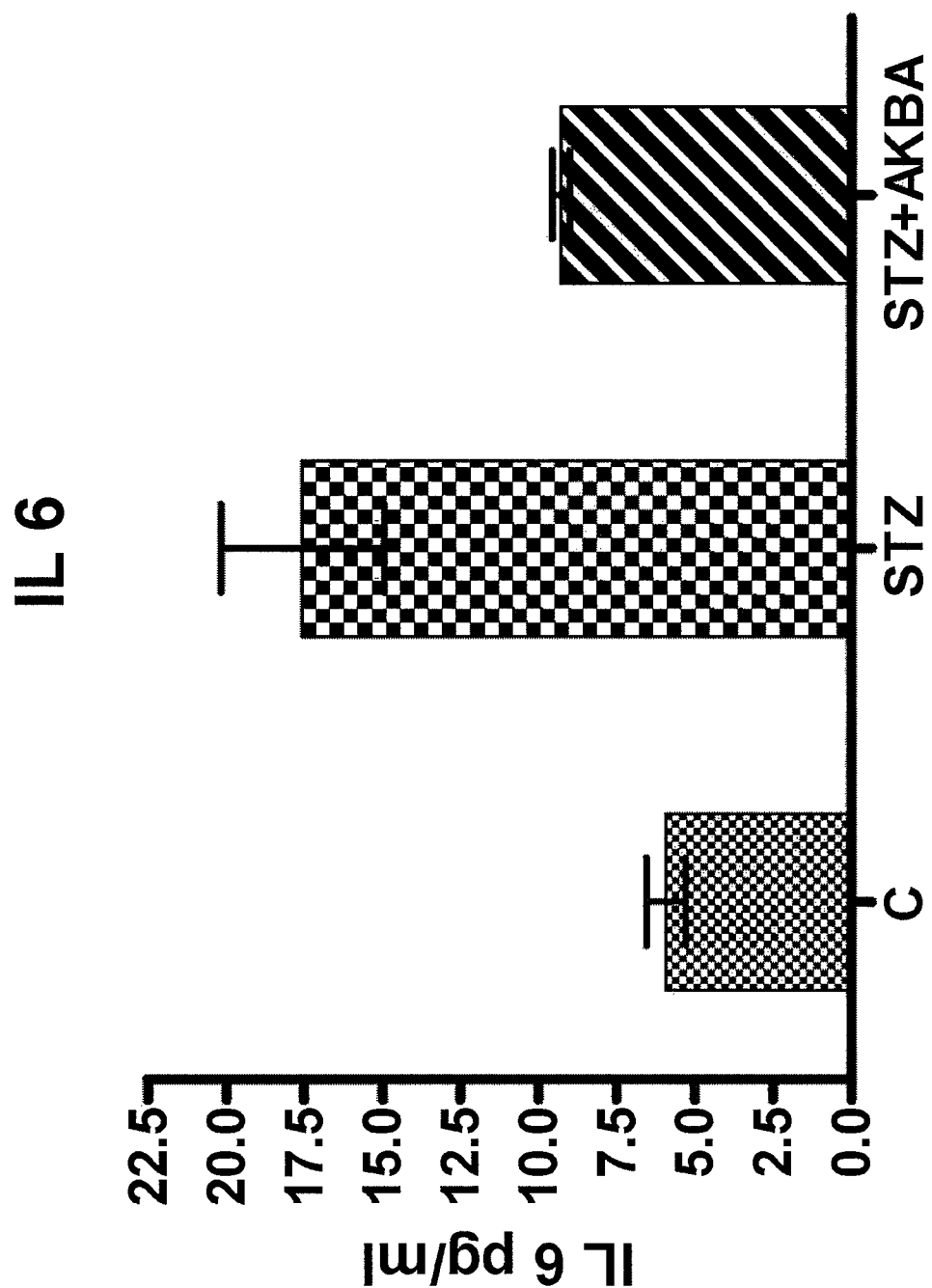
Figure 10E:
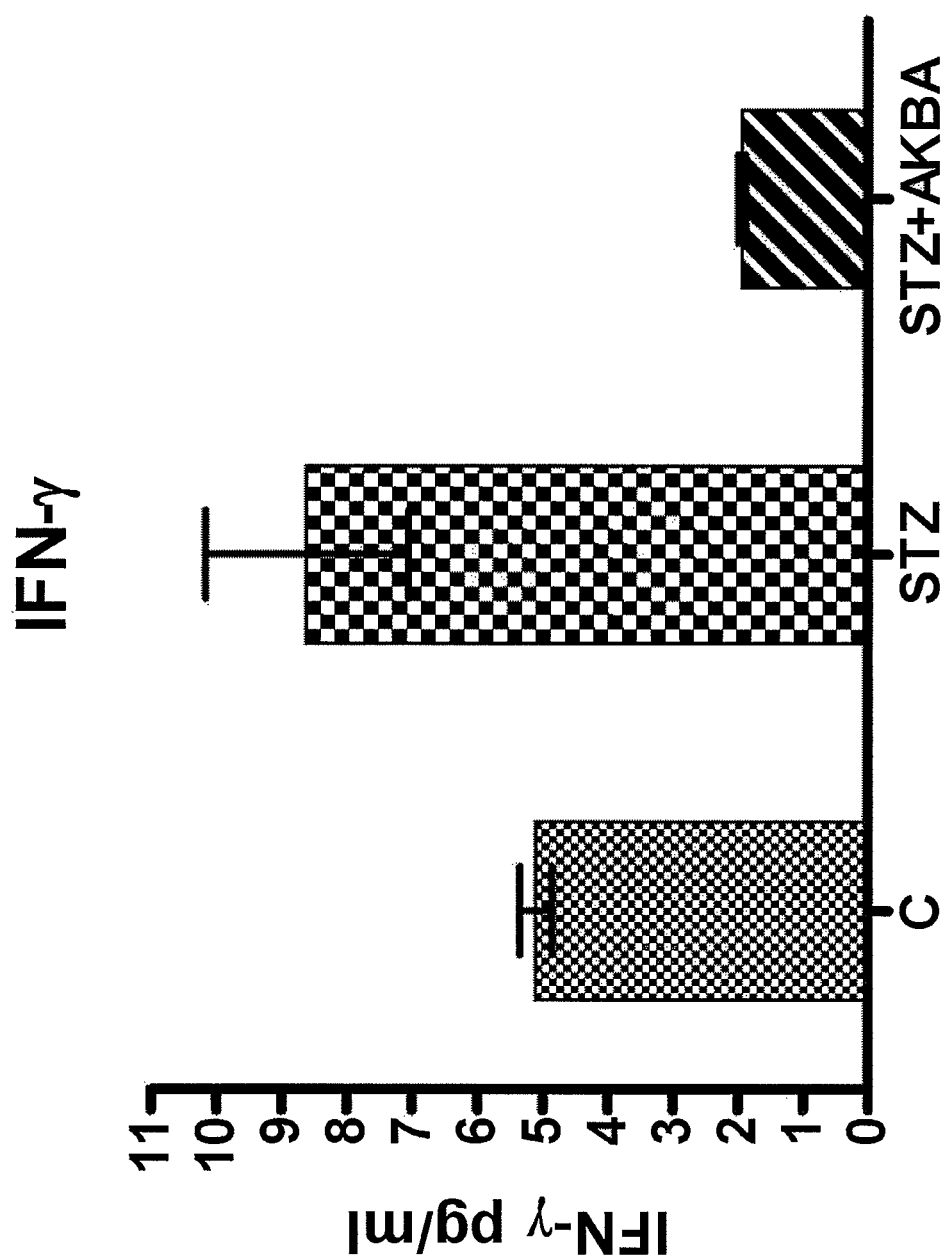
Figure 10F:
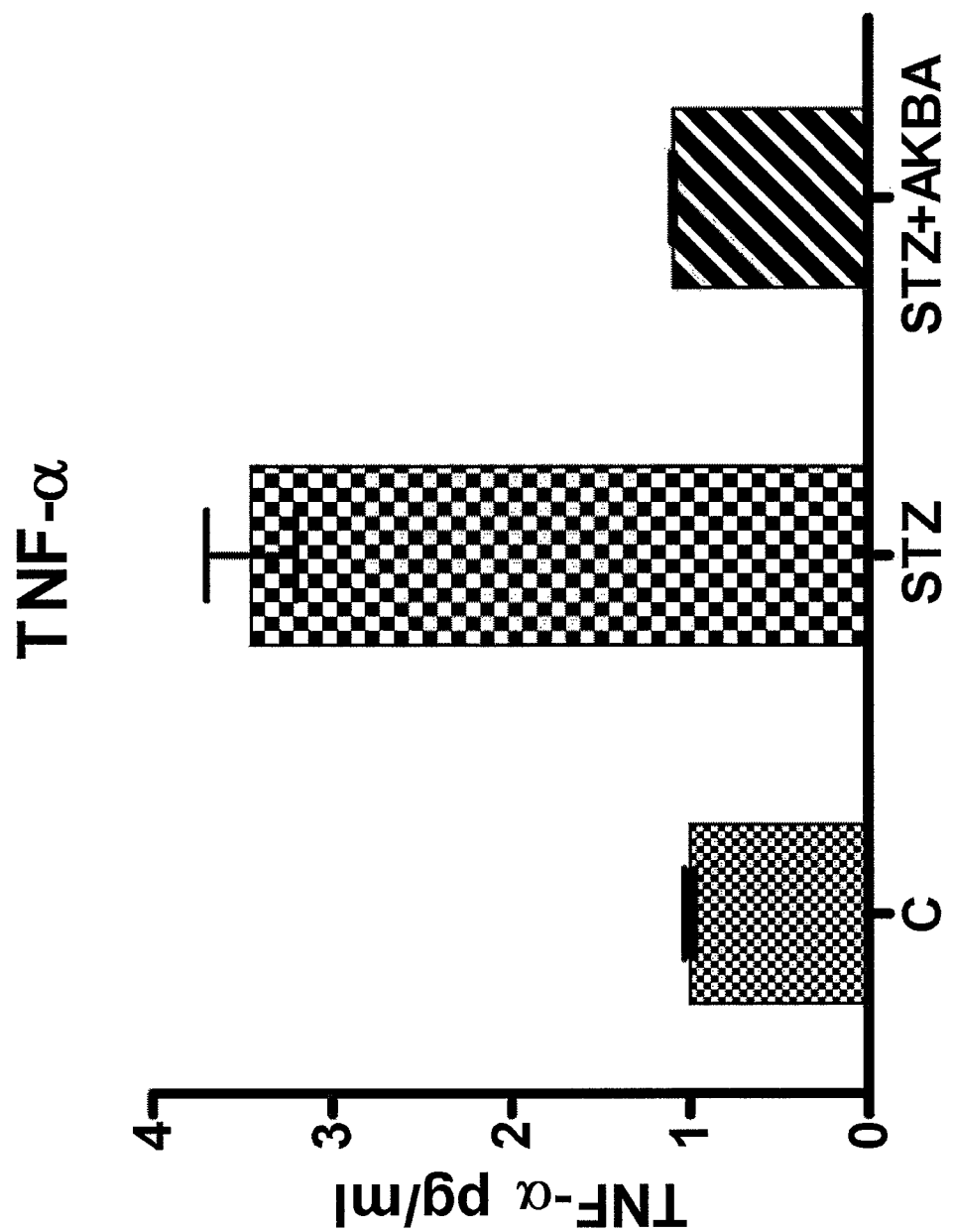
Figure 11A:
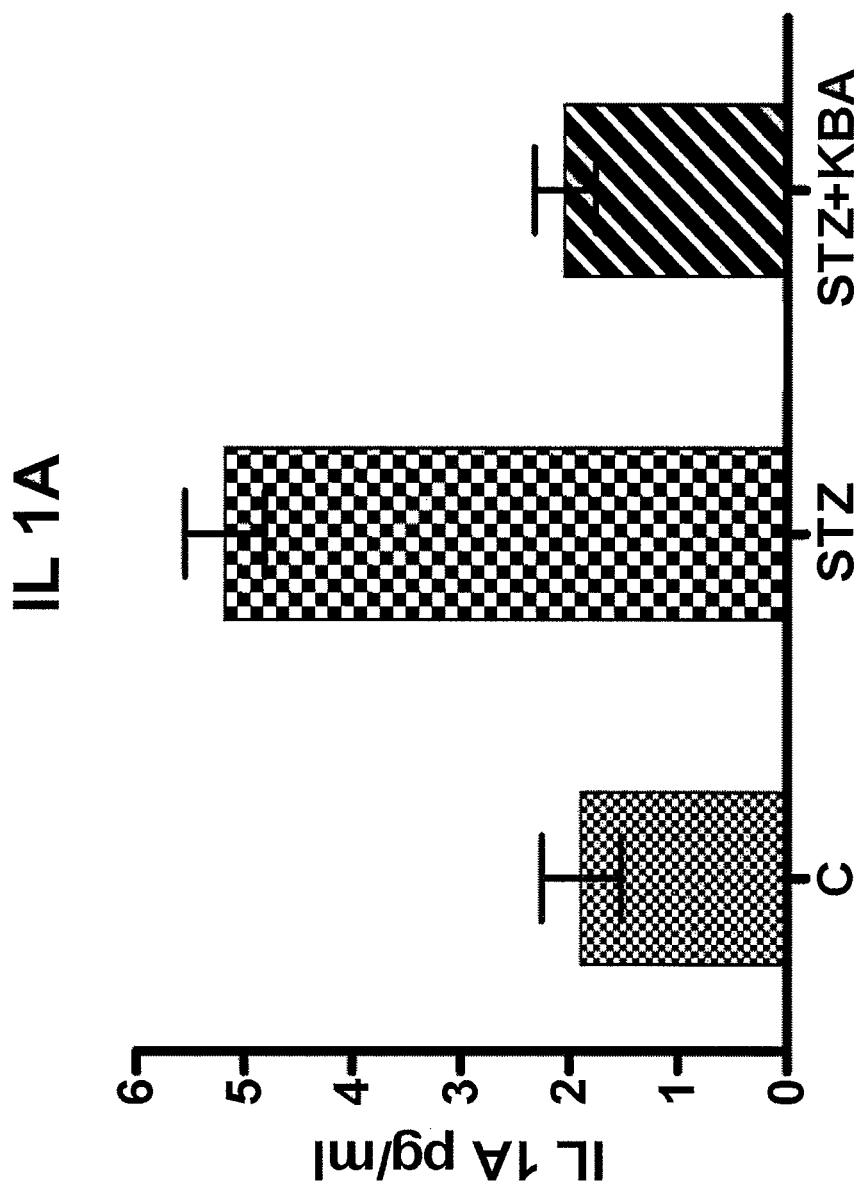
FIGS. 11A-F show the influence of a 10-day intraperitoneal administration of 7.5 mg/kg 11-keto-β-boswellic acid (KBA) on pro-inflammatory cytokines in the serum of STZ-treated mice (C=untreated control group; mean +/− SE; n=3-5).
Figure 11B:
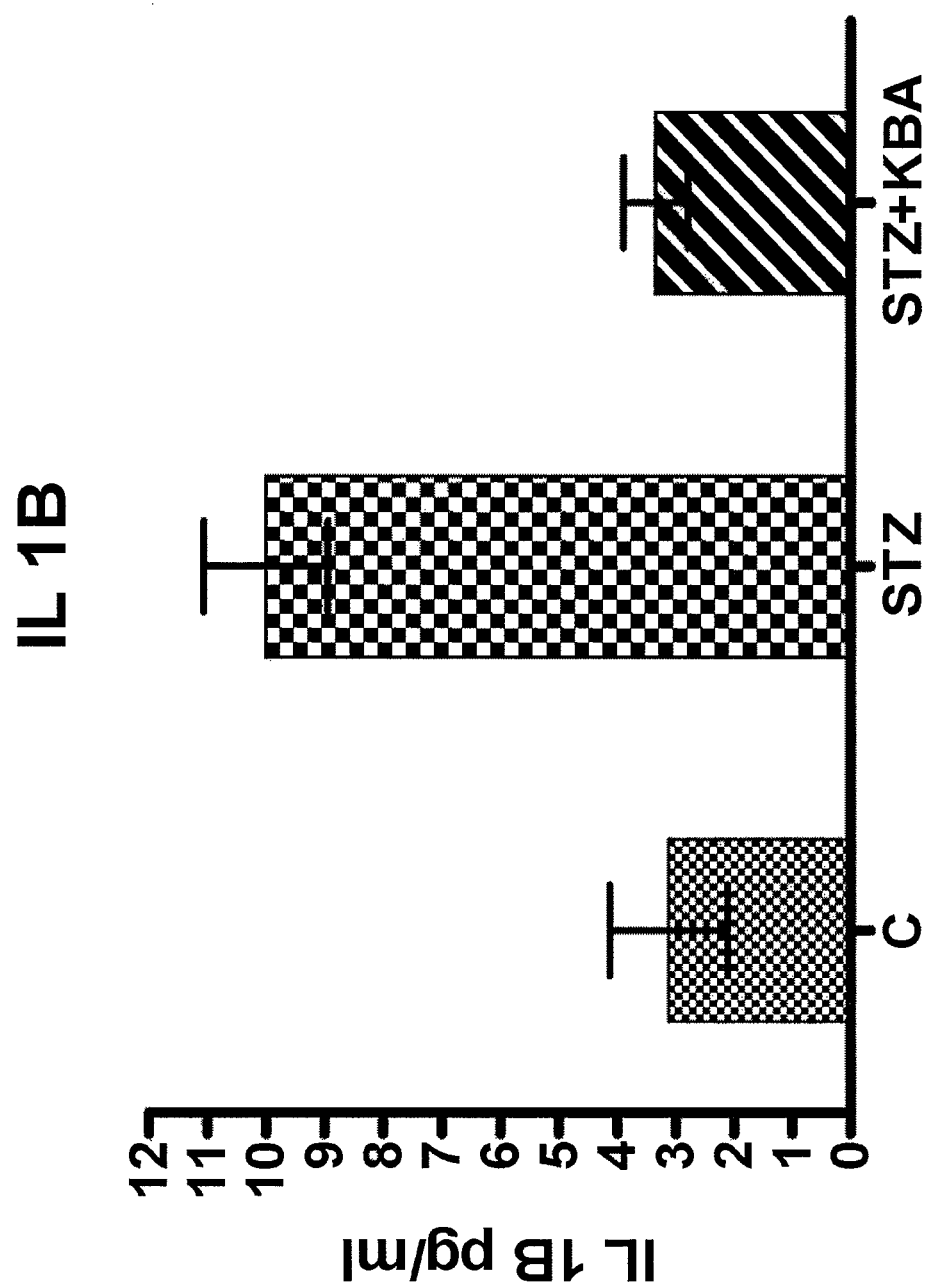
Figure 11C:
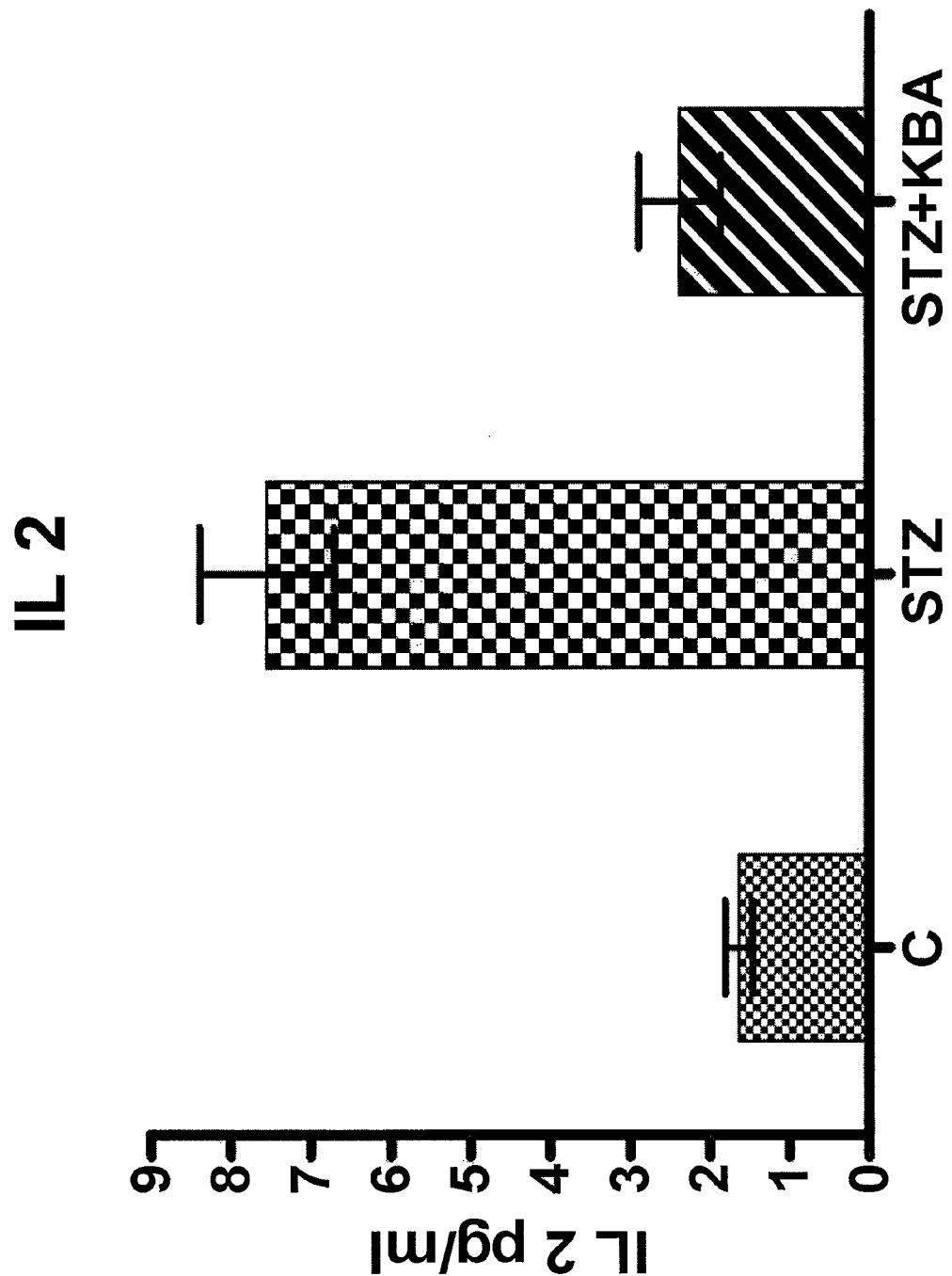
Figure 11D:
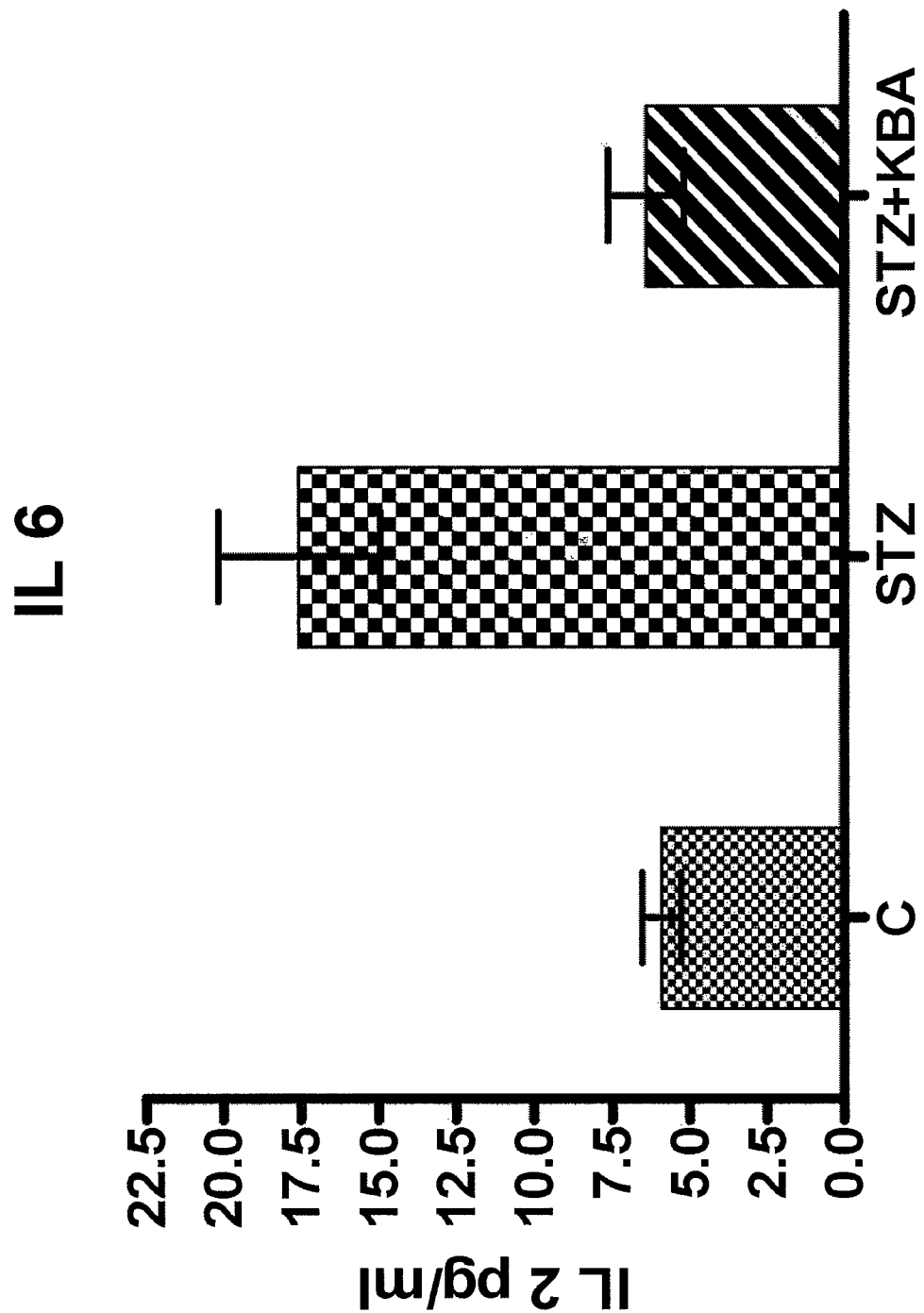
Figure 11E:
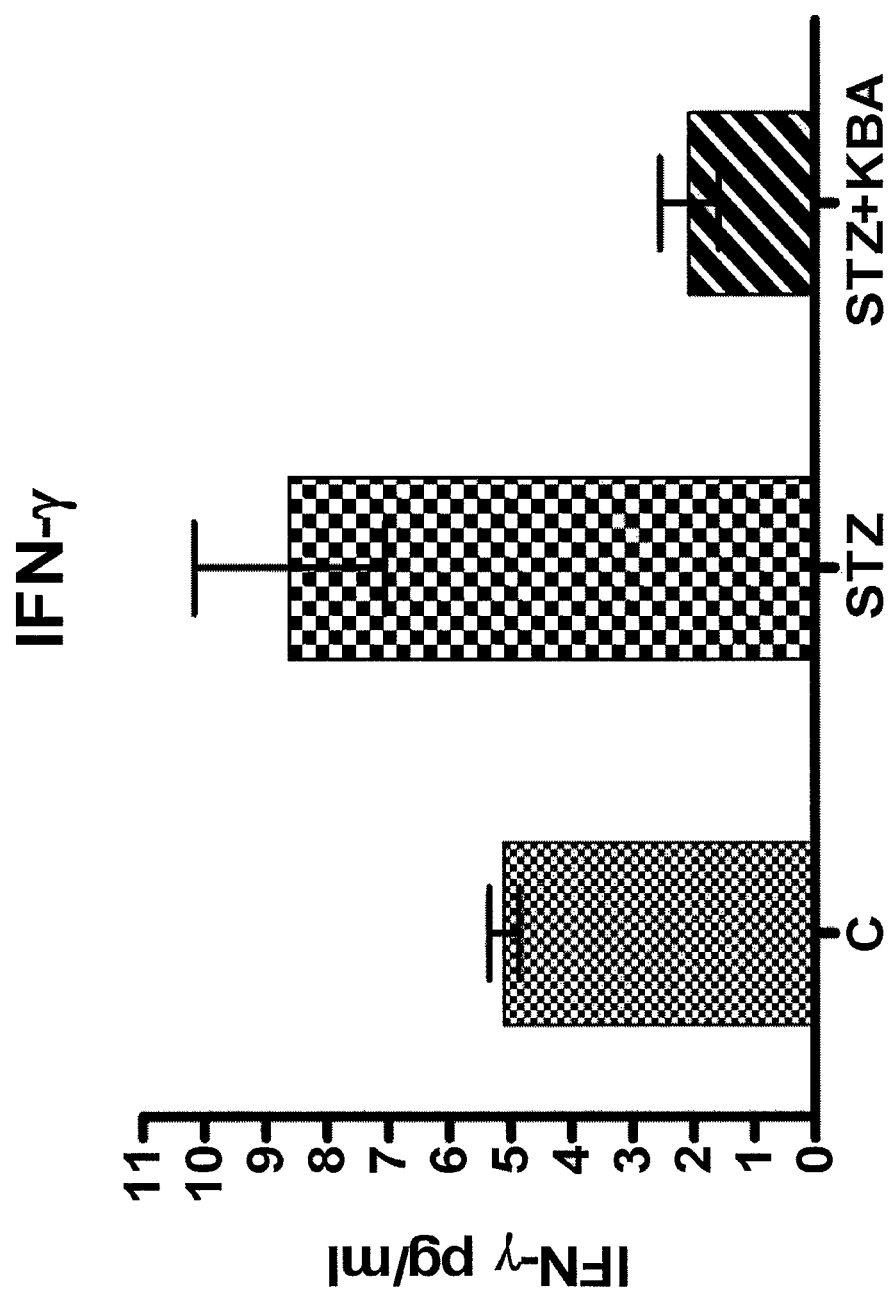
Figure 11F:
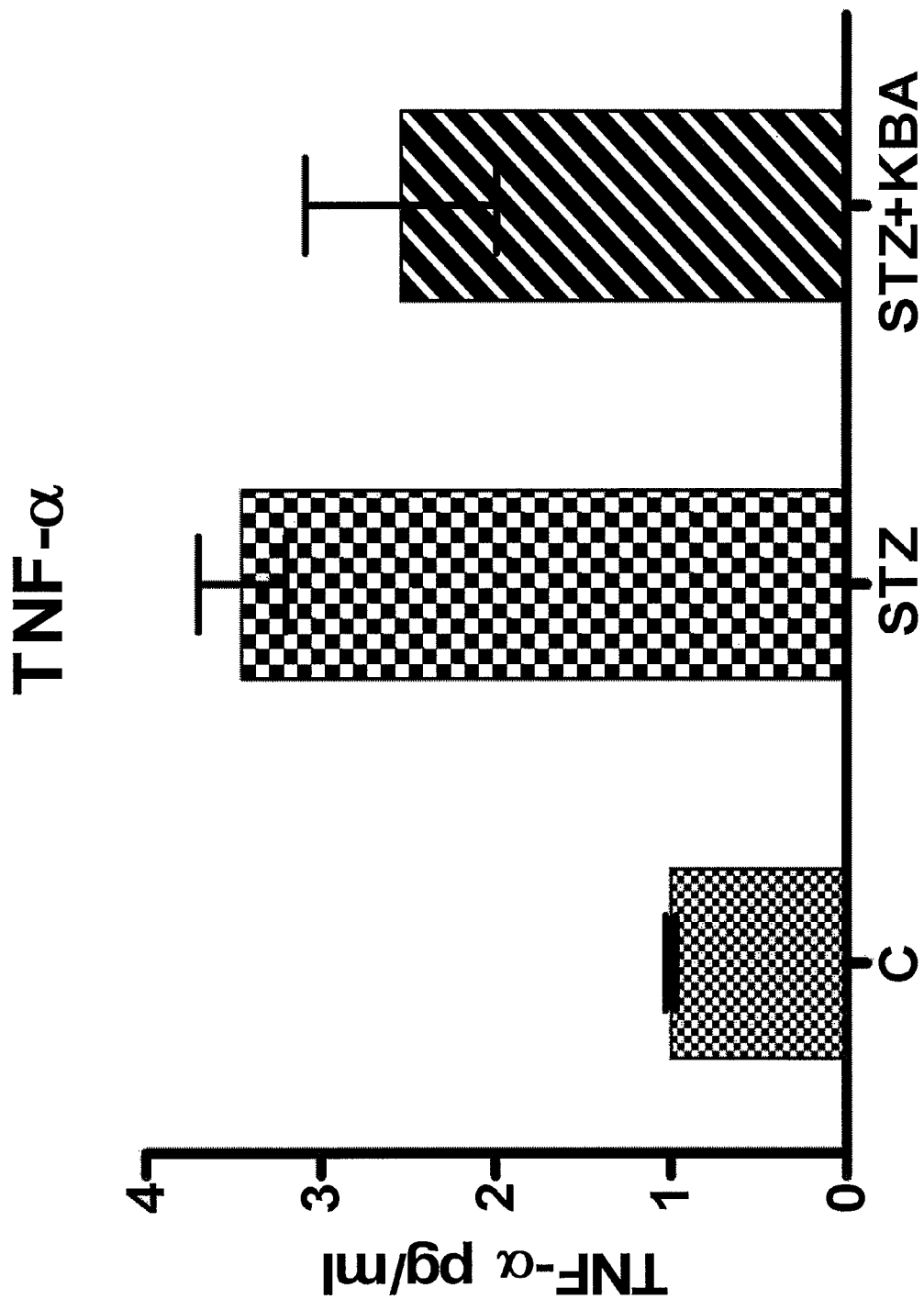

FIG. 8 shows the effect of 7.5 mg/kg KBA on the blood glucose level in MLD-STZ diabetic mice. Like AKBA, KBA reduced the STZ-induced increase of the blood glucose level.

Thus, FIGS. 7 and 8 show that the boswellic acids AKBA and KBA contribute to the prevention of an increase of blood glucose. Further, boswellic acids that are contained in the *boswellia* mixture contribute to this effect so that the anti-diabetic effect of this group of substances is shown.

Example 3

The Effect of BE/KBA on Pro-inflammatory Cytokines in MLD-STZ Diabetic Mice

Cytokines, which are released from the leukocytes, play an important role in chronic inflammation. Among these cytokines, the so-called "pro-inflammatory cytokines", e.g., tumor necrosis factor alpha (TNF-α), interferon gamma (IFN-γ) as well as the interleukins IL-1A, IL-1B, IL-2 and IL-6, are responsible for the induction of inflammation, onset of fever, the permeability of the vessels, the proliferation and activation of lymphocytes as well as the local destruction of tissue, etc. Insulitis is associated with an increase in cytokines in the leukocytes—such as monocytes, macrophages and T-lymphocytes—as well as in the blood.

Male mice were injected i.p. 40 mg/kg STZ for 5 days (STZ group, group A). A second group was, in addition to STZ, treated i.p. with 150 mg/kg BE for 10 days (group STZ+BE, group B). A further group (group C) remained untreated. After 10 days blood samples were taken.

In further tests, 15.0 mg/kg AKBA or 7.5 mg/kg KBA respectively were administered instead of 150 mg/kg BE.

Ten days after daily i.p. injections of 150 mg/kg of *boswellia* extract, of 15.0 mg/kg AKBA or 7.5 mg/kg KBA in MLD-STZ animals (40 mg/kg i.p. for 5 days) the presence of cytokines was determined using the commercially available Multianalyte Array TM Kits (mouse-inflammatory cytokines, SA Bioscience Corporation, USA) according to the instructions on usage provided by the manufacturer. The cytokines IL-1A, IL-1B, IL-2, IFN-γ, IL-6 and TNF-α were ascertained. The test results are shown in FIGS. 7 and 8.

It is well-known that in inflammation, pro-inflammatory cytokines increase in the tissue followed by an infiltration of inflammation cells into the tissue.

The test values shown in FIGS. 9, 10, and 11 show that 10 days after the induction of MLD-STZ diabetes, all cytokines tested were significantly increased in the serum. The additional i.p. administration of BE, AKBA or KBA reduced or prevented the STZ-induced increase in TNF-α (FIGS. 9F, 10F, and 11F), IFN-γ (FIGS. 9E, 10E, and 11E), IL-1A (FIGS. 9A, 10A, and 11A), IL-1B (FIGS. 9B, 10B, and 11B), IL-2 (FIGS. 9C, 10C, and 11C) and IL-6 (FIGS. 9D, 10D, and 11D). The corresponding levels in the serum of the animals tested no longer differed significantly from those of the control group.

In line with the test values described herein, one can assume that the prevention of leukocyte infiltration into the islets of Langerhans, the prevention of apoptosis and the prevention or reduction of hyperglycemia is due to the inhibiting effect of BE, AKBA or KBA on the STZ-induced increase of pro-inflammatory cytokines. Consequently, by the effect of the boswellic acids tested herein as well as by an extract containing the same, damage of the B-cells of the islets of Langerhans can be reduced or prevented.

The data described herein demonstrate that:

STZ causes damage of the morphologic structure and the functions of the islets of Langerhans and leads to the death of B cells. This leads to an increase in the blood glucose level as a consequence of insulin deficiency, e.g., diabetes mellitus on the basis of damage of the islets of Langerhans which may be associated with an inflammatory process in the islets of Langerhans.

These processes can be prevented by administering a mixture of boswellic acids in a *boswellia* extract (BE) or by administering individual boswellic acids.

The effect of the mixtures of boswellic acids is due to the effect of one or more boswellic acids. This can be deduced from the fact that two of the boswellic acids contained in the aforesaid mixture, namely AKBA and KBA, can also individually reduce an increase in blood glucose in response to the diabetogenic agent STZ.

What is claimed is:

1. A method of ameliorating insulitis without treating diabetes mellitus in a subject in need thereof, comprising:
providing the subject in need of treatment for insulitis; and administering to said subject a composition comprising a compound selected from the group consisting of: acetyl-11-keto-β-boswellic acid, 11-keto-β-boswellic acid, β-boswellic acid, acetyl-β-boswellic acid, 9, 11-dehydro-β-boswellic acid, acetyl-9, 11-dehydro -β-boswellic acid, α-boswellic acid, acetyl-α-boswellic acid, 11-dehydro-α-boswellic acid, acetyl-9,11-dehydro-α-boswellic acid, lupeolic acid, acetyl-lupeolic acid, 12-ursene-2-diketone, incensole, incensole acetate, derivatives thereof, esters thereof, pharmaceutically acceptable salts thereof, and combinations thereof, whereby damage to and/or inflammation of the islets of Langerhans and/or damage to the B-cells of the islets of Langerhans is treated, wherein a dose in the range from about 0.4 mg/kg to about 8.0 mg/kg of the composition is administered to the subject.

2. The method according to claim 1, wherein the composition consists of acetyl-11-keto-β-boswellic acid or a pharmaceutically acceptable salt thereof and 11-keto-β-boswellic acid or a pharmaceutically acceptable salt thereof.

3. The method according to claim 2, wherein the composition is in a single dosage form.

4. The method according to claim 3, wherein the single dosage form is formulated for intraperitoneal, oral, buccal, rectal, intramuscular, subcutaneous or intravenous administration.

5. The method according to claim 3, wherein the single dosage form is a tablet, sugar coated tablet, capsule, solution, emulsion, or suppository.

6. The method according to claim 2, wherein the composition further comprises at least one other pharmaceutical substance.

7. The method according to claim 6, wherein the at least one other pharmaceutical substance is selected from the group consisting of an antiphlogistic, an oral antidiabetic, an antioxidant, pentoxifylline, isoxazolene, an interferon, a ganglioside, an α-adrenoceptor antagonist, nicotinamide, dimethylurea, a lipid-lowering agent, and an herbal drug.

8. The method according to claim 7, wherein the oral antidiabetic is selected from the group consisting of a sulfonylurea, a glinide, metformin, an imidazolidinone, a glitazone, an α-glucosidase inhibitor, and a dipeptylpeptidase IV inhibitor.

9. The method according to claim 1, wherein the subject is:
  i) a person with a genetic predisposition for type 1 diabetes and a diabetes-inducing disease caused by a virus selected from the group consisting of mumps virus, coxsackie B virus, rubella virus, measles virus, cytomegalovirus, and influenza virus;
  ii) a person with at least one type 1 diabetic parent or sibling; or
  iii) a person with at least one upregulated diagnostic marker for inflammation of the pancreas.

10. The method according to claim 9, wherein the diagnostic marker is selected from the group consisting of a glutamate decarboxylase, a tyrosine phosphatase IA-2, and an islet cell antibody.

11. The method according to claim 1, wherein the composition comprises 11-keto-β-boswellic acid.

12. The method according to claim 1, wherein the composition comprises acetyl-11-keto-β-boswellic acid.

13. A method of ameliorating insulitis without treating diabetes mellitus in a subject, comprising:
  identifying the subject having insulitis; and
  administering to the subject a composition comprising a compound selected from the group consisting of: acetyl-11-keto-β-boswellic acid, 11-keto-β-boswellic acid, and pharmaceutically acceptable salts thereof, wherein a dose in the range from about 0.4 mg/kg to about 8.0 mg/kg of the composition is administered to the subject.

14. The method according to claim 13, wherein the composition comprises 11-keto-β-boswellic acid.

15. The method according to claim 13, wherein the composition comprises acetyl-11-keto-β-boswellic acid.

16. The method according to claim 13, wherein the composition comprises acetyl-11-keto-β-boswellic acid or a pharmaceutically acceptable salt thereof and 11-keto-β-boswellic acid or a pharmaceutically acceptable salt thereof.

17. The method according to claim 13, wherein the composition is in a single dosage form.

18. The method of claim 1, wherein a dose in the range from about 0.4 mg/kg to about 4.0 mg/kg of the composition is administered to the subject.

19. The method of claim 13, wherein a dose in the range from about 0.4 mg/kg to about 4.0 mg/kg of the composition is administered to the subject.

* * * * *